United States Patent
Minucci et al.

(10) Patent No.: US 8,765,820 B2
(45) Date of Patent: Jul. 1, 2014

(54) TRANYLCYPROMINE DERIVATIVES AS INHIBITORS OF HISTONE DEMETHYLASES LSD1 AND/OR LSD2

(75) Inventors: Saverio Minucci, Opera (IT); Antonello Mai, Rome (IT); Andrea Mattevi, Pavia (IT)

(73) Assignees: Universita Degli Studi di Roma "La Sapienza", Rome (IT); Fondazione IEO, Milan (IT); Universita Degli Studi di Pavia, Pavia (IT); Universita Degli Studi di Milano, Milan (IT)

( * ) Notice: Subject to any disclaimer, the term of this patent is extended or adjusted under 35 U.S.C. 154(b) by 88 days.

(21) Appl. No.: 13/641,715

(22) PCT Filed: Apr. 15, 2011

(86) PCT No.: PCT/EP2011/055990
§ 371 (c)(1),
(2), (4) Date: Oct. 25, 2012

(87) PCT Pub. No.: WO2011/131576
PCT Pub. Date: Oct. 27, 2011

(65) Prior Publication Data
US 2013/0035377 A1    Feb. 7, 2013

Related U.S. Application Data

(60) Provisional application No. 61/325,952, filed on Apr. 20, 2010.

(51) Int. Cl.
*A61K 31/015* (2006.01)
*C07C 329/00* (2006.01)

(52) U.S. Cl.
USPC ............................. 514/765; 564/161

(58) Field of Classification Search
CPC .................. C07C 2101/02; C07C 2101/16
USPC ........................... 514/765; 564/161
See application file for complete search history.

(56) References Cited

PUBLICATIONS

Gooden, D. M., et al: "Facile synthesis of substituted trans-2-arylcyclopropylamine inhibitors of the human histone demethylase LSD1 and monoamine oxidases A and B", Bioorganic & Medicinal Chemistry Letters, Pergamon, Elsevier Science, GB, vol. 18, No. 10, May 15, 2008, pp. 3047-3051.

Binda, Claudia, et al: "Biochemical, structural, and biological evaluation of tranylcypromine derivatives as inhibitors of histone demethylases LSD1 and LSD2", Journal of the American Chemical Society, 132(19), pp. 6827-6833.

*Primary Examiner* — Paul Zarek
(74) *Attorney, Agent, or Firm* — Lucas & Mercanti, LLP

(57) ABSTRACT

Tranylcypromine derivatives useful as therapeutic agents, particularly for the prevention and/or treatment of diseases and conditions associated with the activity of histone demethylases LSD1 and LSD2, such as the diseases characterized by deregulation of gene transcription, cell differentiation and proliferation, e.g. tumors, viral infections, are herein described. These compounds belong to the structural formula (I) wherein A and $R_3$ are as defined in the specification. The invention also relates to the preparation of these compounds, as well as to compositions containing them and to therapeutic use thereof.

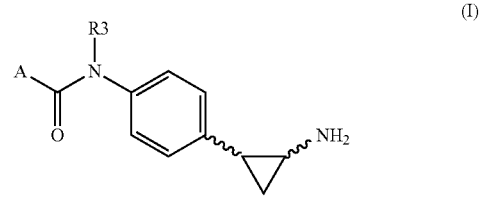

12 Claims, 2 Drawing Sheets

Figure 1:
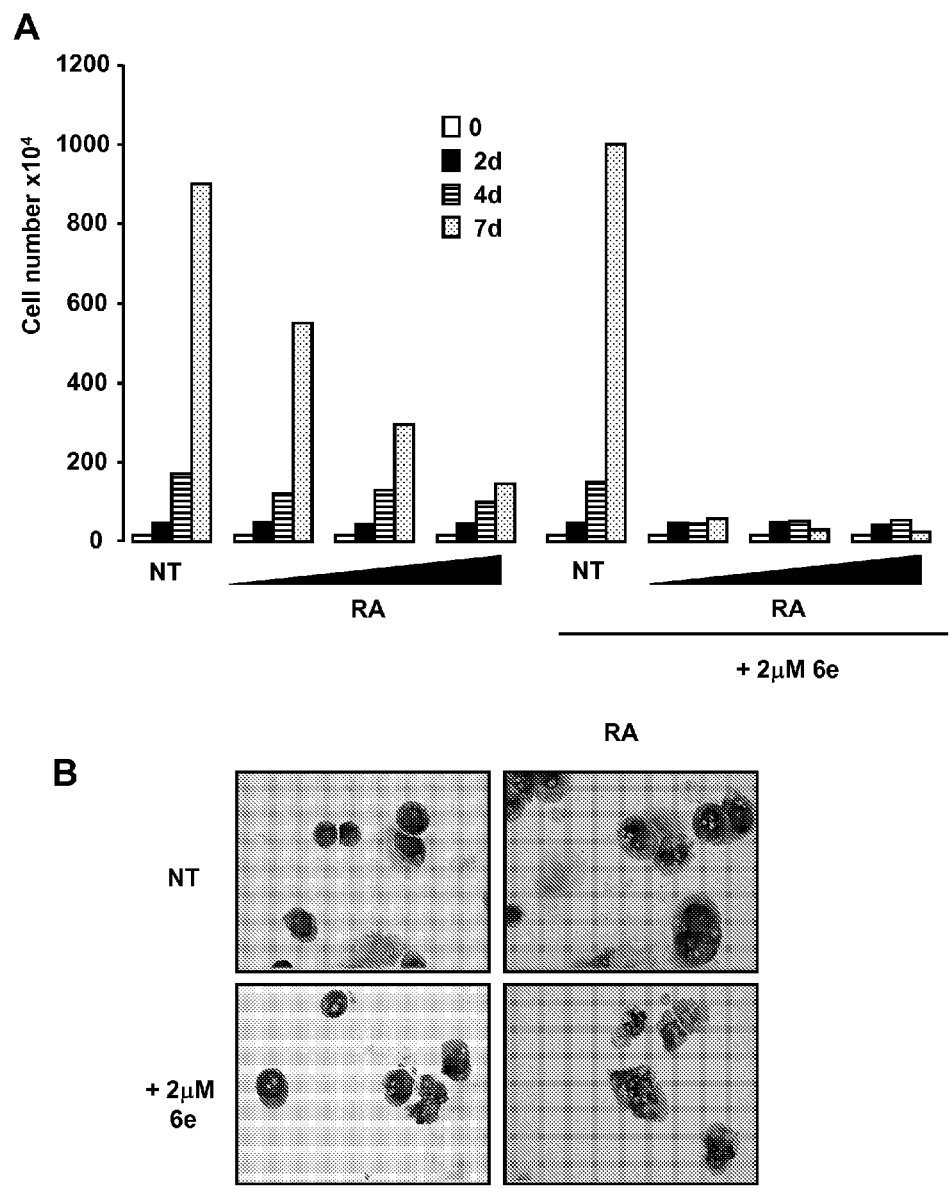

TRANYLCYPROMINE DERIVATIVES AS INHIBITORS OF HISTONE DEMETHYLASES LSD1 AND/OR LSD2

CROSS-REFERENCE TO RELATED APPLICATIONS

This application is a 371 of PCT/EP2011/055990, filed Apr. 15, 2011, which claims the benefit of U.S. Provisional Patent Application No. 61/325,952, filed Apr. 20, 2010, the contents of each of which are incorporated herein by reference.

FIELD OF THE INVENTION

The present invention relates to tranylcypromine derivatives and to their use as therapeutic agents, particularly for the prevention and/or treatment of diseases and conditions associated with the activity of histone demethylases LSD1 and LSD2, such as the diseases characterized by deregulation of gene transcription, cell differentiation and proliferation, e.g. tumors, viral infections. The invention also relates to the preparation of these compounds, as well as to compositions containing them and to therapeutic use thereof.

BACKGROUND OF THE INVENTION

Alterations in the structural and functional states of chromatin are involved in the pathogenesis of a variety of diseases. The biochemical and enzymatic processes that catalyze the insertion and elimination of the post-translational modifications on the nucleosomes have become the subject of research as potential targets for the so-called epigenetic therapies (Urdinguio R G, Sanchez-Mut J V, Esteller M. Epigenetic mechanisms in neurological diseases: genes, syndromes, and therapies. *Lancet Neurol.* 8:1056-1072, 2009). The discovery of an increasing number of histone demethylases has highlighted the dynamic nature of the regulation of histone methylation, a key chromatin modification that is involved in eukaryotic genome and gene regulation. Histone lysine demethylases represent very attractive targets for epigenetic drugs and are gaining increasing attention. A lysine can be mono-, di-, and tri-methylated. Each modification on the same amino acid can specifically exert different biological effects. The recent discovery of histone lysine demethylases has revealed two types of enzymatic mechanisms (Anand R, Marmorstein R. Structure and mechanism of lysine-specific demethylase enzymes. *J. Biol. Chem.* 282:35425-35429, 2007). The iron-dependent enzymes can demethylate lysine side chains in all three methylation states and many demethylases in this family have now been characterized. Conversely, the oxidative chemistry that underlies the function of flavin-dependent histone demethylases makes it impossible for these enzymes to act on a trimethylated lysine and restricts their activity to mono- and di-methylated substrates. Mammals contain two flavoenzyme demethylases: LSD1 and LSD2. LSD1 was the first discovered histone demethylase and is typically (but not always) associated with the co-repressor protein CoREST. LSD1/CoREST can associate to histone deacetylases 1/2 (HDAC1/2) forming a multienzyme unit that is recruited by many chromatin complexes that are typically involved in gene repression regulation (Ballas N, et al. Regulation of neuronal traits by a novel transcriptional complex. *Neuron.* 31:353-365, 2001). LSD1 erases the methyl groups from mono- and di-methyl Lys4 of histone H3, which is a well-characterized gene activation mark. The enzyme is an interesting target for epigenetic drugs as suggested by its overexpression in solid tumors (Schulte J H, et al. Lysine-specific demethylase 1 is strongly expressed in poorly differentiated neuroblastoma: implications for therapy. *Cancer Res* 69:2065-2071, 2009), its role in various differentiation processes (Hu X, et al. LSD1-mediated epigenetic modification is required for TAL1 function and hematopoiesis. *Proc Natl Acad Sci USA* 106:10141-10146, 2009), its involvement in herpes virus infection (Gu H, Roizman B. Engagement of the lysine-specific demethylase/HDAC1/CoREST/REST complex by herpes simplex virus 1. *J Virol* 83:4376-4385, 2009), and its association to HDAC1, a validated drug-target. LSD2 is a more recently discovered demethylase which, like LSD1, displays a strict specificity for mono- and di-methylated Lys4 of H3. However, the biology of LSD2, which remains only partly characterized, proposed to differ from that of LSD1 since LSD2 does not bind CoREST and it has not been found so-far in any LSD1-containing protein complex (Karytinos A, et al. A novel mammalian flavin-dependent histone demethylase. *J Biol Chem* 284:17775-17782, 2009).

LSD1 and LSD2 are multi-domain proteins which share a similar catalytic domain (45% sequence identity) that is structurally homologous with the monoamine oxidases (MAOs) A and B. Tranylcypromine, (±)-trans-2-phenylcyclopropyl-1-amine (tPCPA), a MAO inhibitor used as antidepressive drug, is also able to inhibit LSD1 (Schmidt D M, McCafferty D G. trans-2-Phenylcyclopropylamine is a mechanism-based inactivator of the histone demethylase LSD1. *Biochemistry* 46:4408-4416, 2007).

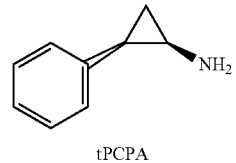

tPCPA

Gooden et at (*Bioorg. Med. Chem. Lett.* 18, 3047-3051, 2008) describes a synthetic route to substituted trans-2-arylcyclopropylamines as inhibitors of LSD1 and MAOs. These derivatives are more than 10 fold more efficient in inhibiting MAO A and B than LSD1.

Culhane et al (*J. Am. Chem. Soc.* 132, 3164-3176, 2010) relates to the hydrazine containing MAO inhibitor phenelzine as a small molecule LSD1 inhibitors.

WO 2010011845 describes a method of treating a viral infection of a host, by administering to the host an inhibitor of the protein LSD1 (an RNAi molecule) and/or a monoamine oxidase inhibitor, e.g. tranylcypromine.

EP 1693062 relates to the use of at least one siRNA ("short interfering RNA") and at least one anti-LSD1 antibody, also in combination with a monoamine oxidase inhibitor, e.g. tranylcypromine, for modulating the activity of LSD1 and controlling the androgen receptor-dependent gene expression.

WO 2010/043721, WO 2010/084160 and WO 2010/143582, WO2011/035941 which were published after the priority date of the present application, disclose phenylcyclopropylamine derivatives capable of selectively inhibiting the function of LSD1. None of disclosed compounds are within the instant invention.

Hence there is a need to identify small molecules as potent and selective inhibitors of the LSD1 and/or LSD2 histone demethylase, which are useful in the prevention or therapy of diseases and conditions associated with the activity of the histone demethylases.

The compounds of the present invention are small molecules endowed with potent histone demethylases inhibitory activity, which are useful in the treatment of a variety of diseases in which deregulation of gene transcription, cell differentiation and proliferation is observed, e.g. tumors, viral infections.

DESCRIPTION OF THE INVENTION

The present invention is directed towards compounds that are endowed with LSD1 and/or LSD2 histone demethylases inhibiting activity and are useful in the prevention or therapy of diseases and conditions associated with the activity of the LSD1 and/or LSD2 histone demethylases. The invention is directed also to methods of preparing said compounds, compositions containing them and therapeutic use thereof.

The invention discovered that tranylcypromine derivatives of general formula (I), and derivatives thereof, are endowed with histone demethylases inhibiting activity.

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

It is therefore an object of the invention a compound of formula (I)

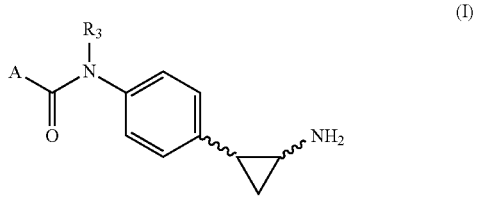

(I)

wherein:

A is R or CH(R$_1$)—NH—CO—R$_2$;

R and R$_2$ are selected from: alkyl, alkenyl, alkynyl, cycloalkyl, aryl, heteroaryl, heterocycloalkyl, cycloalkylalkyloxy, arylalkyloxy, heteroarylalkyloxy, heterocycloalkylalkyloxy, cycloalkylalkyl, arylalkyl, heteroarylalkyl, heterocycloalkylalkyl, cycloalkylalkylamino, arylalkylamino, heteroarylalkylamino, heterocycloalkylalkylamino;

R$_1$ is selected from: alkyl, alkenyl, alkynyl, cycloalkyl, aryl, heteroaryl, heterocycloalkyl, cycloalkylalkyl, arylalkyl, heteroarylalkyl, heterocycloalkylalkyl;

R$_3$ is H, lower alkyl;

as well as its isomers, tautomers, racemic forms, enantiomers, diastereomers, epimers, polymorphs, solvates, mixtures thereof, prodrugs, and the pharmaceutically acceptable salts thereof.

The term "alkyl" refers to a fully saturated straight or branched saturated hydrocarbon chain having one to 10 carbon atoms. Examples include, but are not limited to, methyl, ethyl, n-propyl, isopropyl, t-butyl, pentyl, hexyl, heptyl, octyl, nonyl, decyl and the like. "Lower alkyl" or "C$_1$-C$_6$ alkyl" have similar meanings except that they contain from one to six carbon atoms.

The term "alkenyl" refers to a straight or branched hydrocarbon chain having from two to ten carbon atoms and at least one carbon-carbon double bond. Examples include, but are not limited to, ethenyl, 2-propenyl, isobutenyl and the like.

The term "alkynyl" refers to a straight or branched hydrocarbon chain having from two to ten carbon atoms and at least one carbon-carbon triple bond. Examples include, but are not limited to, ethynyl, 2-propynyl, isobutynyl and the like.

The term "cycloalkyl" refers to any non-aromatic carbocyclic ring system of 1 or 2 ring moieties. A cycloalkyl group can have one or more carbon-carbon double bonds in the ring so long as the ring is not rendered aromatic by their presence. Examples of cycloalkyl groups include, but are not limited to, (C3-C7)cycloalkyl groups, such as cyclopropyl, cyclobutyl, cyclopentyl, cyclohexyl and cycloheptyl, and saturated cyclic and bicyclic terpenes and (C3-C7)cycloalkenyl groups, such as cyclopropenyl, cyclobutenyl, cyclopentenyl, cyclohexenyl and cycloheptenyl, and unsaturated cyclic and bicyclic terpenes.

The term "aryl" refers to any aromatic carbocyclic ring system of 1 or 2 ring moieties, either fused or linked to each other through a single bond. Suitable aryl groups include, but are not limited to, phenyl, α- or β-naphthyl, biphenyl, indanyl, indenyl, and the like.

The term "heteroaryl" refers to monocyclic- or polycyclic aromatic rings comprising carbon atoms and one or more heteroatoms, preferably, 1 to 3 heteroatoms, independently selected from nitrogen, oxygen, and sulfur. As is well known to those skilled in the art, heteroaryl rings have less aromatic character than their all-carbon counter parts. Thus, for the purposes of the invention, a heteroaryl group need only have some degree of aromatic character. Illustrative examples of heteroaryl groups include, but are not limited to, furyl, benzofuranyl, benzodioxolyl, thienyl, benzothiophenyl, pyridinyl, pyridyl-N-oxide, pyrimidinyl, pyridazinyl, pyrazinyl, pyrazolyl, oxazolyl, thiazolyl, isoxazolyl, quinolyl, (1,2,3,)- and (1,2,4)-triazolyl, tetrazolyl, triazinyl, pyrrolyl, imidazolyl, imidazo[1,2-a]pyridin-3-yl, indazolyl, isothiazolyl, indolyl, benzoimidazolyl, benzotriazolyl, benzoxazolyl, oxadiazolyl, thiadiazolyl, and the like.

The term "heterocycloalkyl" refers to a non-aromatic monocyclic or polycyclic ring comprising carbon and hydrogen atoms and at least one heteroatom, preferably, 1 to 4 heteroatoms selected from nitrogen, oxygen, and sulfur. A heterocycloalkyl group can have one or more carbon-carbon double bonds or carbon-heteroatoms double bonds in the ring as long as the ring is not rendered aromatic by their presence. Examples of heterocycloalkyl groups include, but are not limited to, aziridinyl, morpholinyl, thiomorpholinyl, piperidinyl, piperazinyl, thiazolidinyl, oxazolidinyl, tetrahydrothienyl, dihydrofuranyl, tetrahydrofuranyl, tetrahydrothiofuranyl, tetrahydropyranyl, pyrazolidinyl, 1,3-dioxolanyl, pyrrolidinyl, pyranyl, dihydropyranyl, isoxazolidinyl, imidazolidinyl and the like. A heterocycloalkyl group can be unsubstituted or substituted with one or two substituents.

The term "cycloalkylalkyloxy" refers to the group —O-(alkyl)-(cycloalkyl), wherein cycloalkyl and alkyl are defined above.

The term "arylalkyloxy" refers to the group —O-(alkyl)-(aryl), wherein aryl and alkyl are defined above.

The term "heteroarylalkyloxy" refers to the group —O-(alkyl)-(heteroaryl), wherein heteroaryl and alkyl are defined above.

The term "heterocycloalkylalkyloxy" refers to the group —O-(alkyl)-(heterocycloalkyl), wherein heterocycloalkyl and alkyl are defined above.

The term "cycloalkylalkyl" refers to an alkyl group substituted with a cycloalkylalkyl group, wherein alkyl and cycloalkylalkyl are defined above.

The term "arylalkyl" refers to an alkyl group substituted with an aryl group, wherein alkyl and aryl are defined above.

The term "heteroarylalkyl" refers to an alkyl group substituted with an heteroaryl group, wherein alkyl and heteroaryl are defined above.

The term "heterocycloalkylalkyl" refers to an alkyl group substituted with an heterocycloalkyl group, wherein alkyl and heterocycloalkyl are defined above.

The term "cycloalkylalkylamino" refers to an amino group substituted with at least one cycloalkylalkyl group, as defined herein.

The term "arylalkylamino" refers to an amino group substituted with at least one arylalkyl group, as defined herein.

The term "heteroarylalkylamino" refers to an amino group substituted with at least one heteroarylalkyl group, as defined herein.

The term "heterocycloalkylalkylamino" refers to an amino group substituted with at least one heterocycloalkylalkyl group, as defined herein.

Any of the above alkyl, alkenyl, alkynyl, cycloalkyl, aryl, heteroaryl, heterocycloalkyl groups may be optionally further substituted in any of their free positions by one or more groups, for instance 1 to 6 groups, selected from: halogen, carboxy, cyano, alkyl, polyfluorinated alkyl, alkenyl, alkynyl, cycloalkyl, aryl, heteroaryl, alkyl-heteroaryl, heteroarylalkyl, amino-alkyl, amino groups and derivatives thereof, such as, for instance, alkylamino, dialkylamino, arylamino, diarylamino, ureido, alkylureido or arylureido; carbonylamino groups and derivatives thereof, such as, for instance, formylamino, alkylcarbonylamino, alkenylcarbonylamino, arylcarbonylamino, alkoxycarbonylamino; hydroxy groups and derivatives thereof, such as, for instance, alkoxy, polyfluorinated alkoxy, aryloxy, heteroaryloxy, alkylcarbonyloxy, arylcarbonyloxy, or cycloalkyloxy; carbonyl groups and derivatives thereof, such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl, hydroxamic acid; sulfurated derivatives, such as, for instance, alkylthio, arylthio, alkylsulfonyl, arylsulfonyl, alkylsulfinyl, arylsulfinyl, arylsulfonyloxy, aminosulfonyl, alkylaminosulfonyl or dialkylaminosulfonyl.

In their turn, whenever appropriate, each of the above substituents may be further substituted by one or more of the aforementioned groups.

The term "halogen" refers to fluorine, chlorine, bromine or iodine atom.

The term "alkoxy" refers to the group —O-(alkyl), wherein alkyl is defined above.

The terms "polyfluorinated alkyl" or "polyfluorinated alkoxy" refer to any straight or branched C1-C6 alkyl or alkoxy group as defined above, wherein more than one hydrogen atom is replaced by fluorine atoms such as, for instance, trifluoromethyl, trifluoromethoxy, 2,2,2-trifluoroethyl, 2,2,2-trifluoroethoxy, 1,2-difluoroethyl, 1,1,1,3,3,3-hexafluoropropyl-2-yl, and the like.

From all of the above, it is clear to the skilled man that any group which name has been identified as a composite name such as, for instance, alkylheteroaryl, alkylthio, arylthio, amino-alkyl, alkylamino, dialkylamino, arylamino, diarylamino, alkylureido, arylureido, alkylcarbonylamino, alkenylcarbonylamino, arylcarbonylamino, aryloxy, arylalkyloxy, alkylcarbonyloxy, alkoxycarbonylamino; heteroaryloxy, arylcarbonyloxy; alkylcarbonyl, arylcarbonyl, alkoxycarbonyl, aryloxycarbonyl, cycloalkyloxycarbonyl, aminocarbonyl, alkylaminocarbonyl, dialkylaminocarbonyl, alkylsulfonyl, arylsulfonyl, alkylsulfinyl, arylsulfinyl, arylsulfonyloxy, aminosulfonyl, alkylaminosulfonyl or dialkylaminosulfonyl and the like, has to be intended as conventionally construed from the parts to which they derive. So far, as an example, the term alkoxycarbonyl stands for a radical containing an alkoxy radical, as defined above, attached via an oxygen atom to a carbonyl radical.

The formulae include one or more "〰〰" to indicate all possible configurations: cis, trans, (R), (S).

The term "acylating agent" refers to a reactive derivative of a carboxylic acid which is capable in the instant process of coupling the acid to an amino group by an amide linkage. Examples of acylating agent include, but are not limited to, organic acyl halides, organic acid anhydrides, carboxylic acids, esters, mixed carboxylic-sulfonic acid anhydrides.

The term "about" encompasses the range of experimental error that may typically occurs in a measurement.

The term "pharmaceutically acceptable salts" refers to the relatively non-toxic mineral and organic acid-addition salts of the compounds of the present invention. These salts may be prepared in situ during the final isolation and purification of the compounds. In particular, the acid-addition salts may be prepared by separately reacting the purified compound in its purified form with an organic or inorganic acid and isolating the salt thus formed. The resulting salts are, for example, hydrochlorides, hydrobromides, sulfates, hydrogenosulfates, dihydrogenophosphates, methane sulfonates, citrates, oxalates, maleates, fumarates, succinates, trifluoroacetates, 2-naphtalenesulfonates, para-toluenesulfonates.

It will be apparent to those skilled in the art that the compounds of general formula (I) may contain asymmetric centers. Therefore the invention also includes the optical stereoisomers and mixtures thereof. Where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion, including racemates, are encompassed within the scope of the present invention. The present invention also relates to the all the isomers and their admixtures, tautomeric forms, racemic forms, enantiomers, diastereoisomers, epimers, as well as their crystalline forms, including their polymorphic forms and mixtures thereof. Some of the compounds are solvated with a stoichiometric or non-stoichiometric amount of one or more solvent molecules (e.g., water, ethanol) as such they are also intended to be encompassed within the scope of the invention.

In cases when compounds may exist in tautomeric forms, each form is contemplated as being included within this invention whether existing in equilibrium or predominantly in one form. Likewise, the metabolites and the pharmaceutically acceptable bio-precursors (otherwise referred to as pro-drugs) of the compounds of formula (I) are included within the scope of, and suitable for use in, the present invention.

So-called "prodrugs" of the compounds of formula (I) are also within the scope of the invention. Thus certain derivatives of compounds of formula (I), which may have little or no pharmacological activity themselves can, when administered into the body, be converted into compounds of formula (I) having the desired activity, for example, by hydrolytic cleavage. Pro-drugs in accordance with the invention can, for example, be produced by replacing appropriate functionalities present in the compounds of formula (I) with certain moieties known to those skilled in the art as pro-moieties as described, for example, in Design of Prodrugs by H. Bundgaard (Elsevier, 1985) or in Prodrugs: design and clinical applications by Jarkko Rautio et al. (Nature reviews drug discovery, volume 7, March 2008, 255-270).

In a preferred embodiment, the invention provides a compound of formula (I), wherein:

A is R; preferably alkyl, aryl, arylalkyloxy, arylalkyl, each of which is optionally substituted;

$R_3$ is H;

as well as its isomers, tautomers, racemic forms, enantiomers, diastereomers, epimers, polymorphs, solvates, mixtures thereof, prodrugs and the pharmaceutically acceptable salts thereof.

In another preferred embodiment, the invention provides a compound of formula (I), wherein:

$R_3$ is H;

A is $CH(R_1)$—NH—CO—$R_2$; preferably, independently or in any combination:

$R_1$ is alkyl, aryl, heteroaryl, cycloalkylalkyl, arylalkyl, heteroarylalkyl, each of which is optionally substituted;

$R_2$ is arylalkyloxy, heteroarylalkyloxy, each of which is optionally substituted;

as well as its isomers, tautomers, racemic forms, enantiomers, diastereomers, epimers, polymorphs, solvates, mixtures thereof, prodrugs and the pharmaceutically acceptable salts thereof.

In another preferred embodiment, the invention provides a compound of formula (I), wherein:

$R_3$ is —$CH_3$;

A is $CH(R_1)$—NH—CO—$R_2$; preferably, independently or in any combination:

$R_1$ is alkyl, aryl, heteroaryl, cycloalkylalkyl, arylalkyl, heteroarylalkyl, each of which is optionally substituted;

$R_2$ is arylalkyloxy, heteroarylalkyloxy, each of which is optionally substituted;

as well as its isomers, tautomers, racemic forms, enantiomers, diastereomers, epimers, polymorphs, solvates, mixtures thereof, prodrugs and the pharmaceutically acceptable salts thereof.

For a reference to any specific compound of formula (I) of the invention, optionally in the form of a pharmaceutically acceptable salt, see the following experimental section.

Specific, non limiting examples of compounds of formula (I) are shown in the following table (Table 1):

TABLE 1

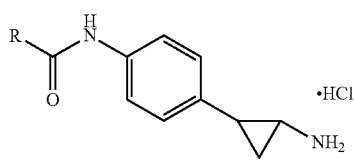

5a-h

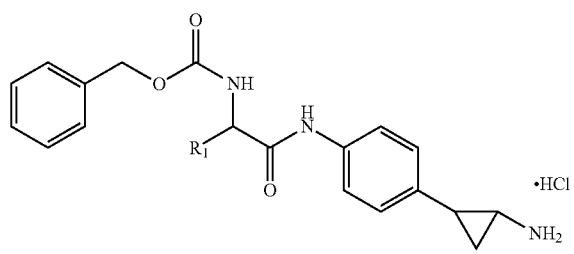

6a-m

| compd | lab code | R | $R_1$ | Name (all as hydrochlorides) |
|---|---|---|---|---|
| 5a | MC2574 | ![benzyloxy] | — | trans benzyl 4-(2-aminocyclopropyl)phenylcarbamate |
| 5b | MC2584 | ![phenyl] | — | trans N-(4-(2-aminocyclopropyl)phenyl)benzamide |
| 5c | MC2634 | ![1-naphthyl] | — | trans N-(4-(2-aminocyclopropyl)phenyl)-1-naphthamide |
| 5d | MC2653 | ![2-naphthyl] | — | trans N-(4-(2-aminocyclopropyl)phenyl)-2-naphthamide |

TABLE 1-continued

| | | | | |
|---|---|---|---|---|
| 5e | MC2652 | (biphenyl-CH2-) | — | trans N-(4-(2-aminocyclopropyl)phenyl)biphenyl-4-carboxamide |
| 5f | MC2639 | (PhCH2CH2-) | — | trans N-(4-(2-aminocyclopropyl)phenyl)-2-phenylacetamide |
| 5g | MC2645 | (naphthalen-1-yl-CH2CH2-) | — | trans N-(4-(2-aminocyclopropyl)phenyl)-2-(naphthalen-1-yl)acetamide |
| 5h | MC2646 | (naphthalen-2-yl-CH2CH2-) | — | trans N-(4-(2-aminocyclopropyl)phenyl)-2-(naphthalen-2-yl)acetamide |
| 6a | MC2707 | — | (isopropyl) | trans benzyl 1-(4-(2-aminocyclopropyl)phenylamino)-3-methyl-1-oxobutan-2-ylcarbamate |
| 6b | MC2663 | — | (isobutyl) | trans benzyl 1-(4-(2-aminocyclopropyl)phenylamino)-4-methyl-1-oxopentan-2-ylcarbamate |
| 6c | MC2708 | — | (cyclohexylmethyl) | trans benzyl 1-(4-(2-aminocyclopropyl)phenylamino)-3-cyclohexyl-1-oxopropan-2-ylcarbamate |
| 6d | MC2633 | — | (phenyl) | trans benzyl 2-(4-(2-aminocyclopropyl)phenylamino)-2-oxo-1-phenylethylcarbamate |
| 6e | MC2580 | — | (benzyl) | trans benzyl 1-(4-(2-aminocyclopropyl)phenylamino)-1-oxo-3-phenylpropan-2-ylcarbamate |
| 6f | MC2764 | — | (4-bromobenzyl) | trans benzyl 1-(4-(2-aminocyclopropyl)phenylamino)-3-(4-bromophenyl)-1-oxopropan-2-ylcarbamate |

TABLE 1-continued

| | | | | |
|---|---|---|---|---|
| 6g | MC2632 | — | 4-ethyl-methoxybenzene group | trans benzyl 1-(4-(2-aminocyclopropyl)phenylamino)-3-(4-methoxyphenyl)-1-oxopropan-2-ylcarbamate |
| 6h | MC2662 | — | 2-phenylethyl group | trans benzyl 1-(4-(2-aminocyclopropyl)phenylamino)-1-oxo-4-phenylbutan-2-ylcarbamate |
| 6i | MC2698 | — | 1,1-diphenylethyl group | trans benzyl 1-(4-(2-aminocyclopropyl)phenylamino)-1-oxo-3,3-diphenylpropan-2-ylcarbamate |
| 6j | MC2687 | — | 1-ethylnaphthalene group | trans benzyl 1-(4-(2-aminocycylpropyl)phenylamino)-3-(napththalen-1-yl)-1-oxopropan-2-ylcarbamate |
| 6k | MC2688 | — | 2-ethylnaphthalene group | trans benzyl 1-(4-(2-aminocyclopropyl)phenylamino)-3-(naphthalen-2-yl)-1-oxopropan-2-ylcarbamate |
| 6l | MC2581 | — | 3-ethylindole group | trans benzyl 1-(4-(2-aminocyclopropyl)phenylamino)-4-(1H-indol-3-yl)-1-oxobutan-2-ylcarbamate |
| 6m | MC2699 | — | 3-ethylbenzo[b]thiophene group | trans benzyl 1-(4-(2-aminocyclopropyl)phenylamino)-4-(benzo[b]thiophen-3-yl)-1-oxobutan-2-ylcarbamate |
| 7 | MC2765 | 4-bromobenzyl carbamate structure with phenyl and aminocyclopropyl-phenyl groups ·HCl | | trans 4-bromobenzyl 1-(4-(2-aminocyclopropyl)phenylamino)-1-oxo-3-phenylpropan-2-ylcarbamate |

TABLE 1-continued

| # | ID | Structure | Name |
|---|---|---|---|
| 8 | MC2829 | 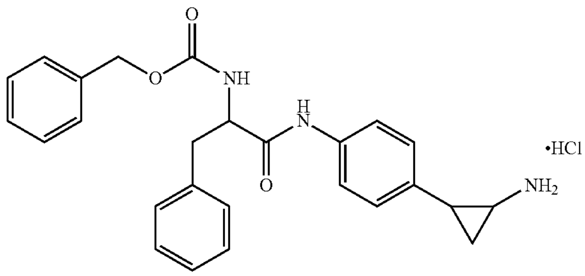 [SMILES: NC1CC1c1ccc(NC(=O)C(Cc2ccccc2)NC(=O)OCc2ccccc2)cc1 ; Cl] | cis benzyl 1-(4-(2-aminocyclopropyl)phenylamino)-1-oxo-3-phenylpropan-2-ylcarbamate ·HCl |
| 9 | MC2575 | 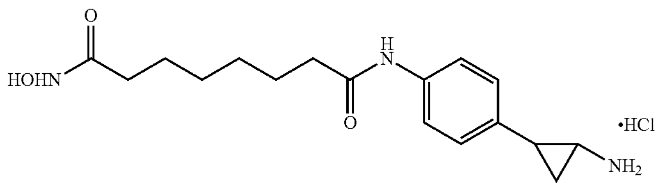 | trans $N^1$-(4-(2-aminocyclopropyl)phenyl)-$N^8$-hydroxyoctanediamide ·HCl |
| 12 | MC3043 | 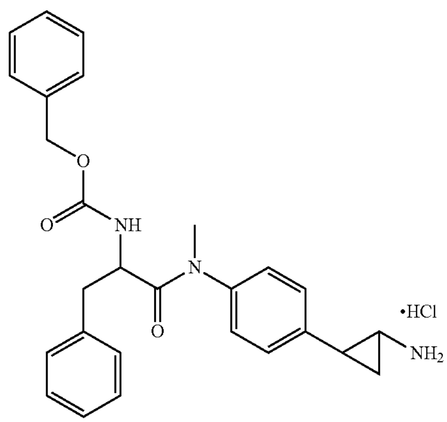 [SMILES: CN(C(=O)C(Cc1ccccc1)NC(=O)OCc1ccccc1)c1ccc(C2CC2N)cc1 ; Cl] | trans benzyl 1-((4-(2-aminocyclopropyl)phenyl)(methyl)amino)-1-oxo-3-phenylpropan-2-ylcarbamate ·HCl |
| 16 | MC3020 | 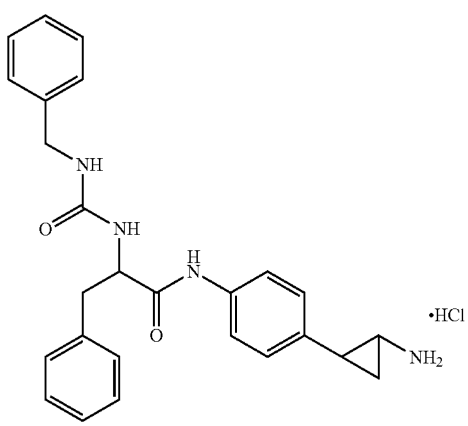 [SMILES: NC1CC1c1ccc(NC(=O)C(Cc2ccccc2)NC(=O)NCc2ccccc2)cc1 ; Cl] | trans N-(4-(2-aminocyclopropyl)phenyl)-2-(3-benzylureido)-3-phenylpropanamide ·HCl |

Isomers, tautomers, racemic forms, enantiomers, diastereomers, polymorphs, solvates, mixtures, prodrugs and the pharmaceutically acceptable salts thereof of compounds described in Table 1 are still within the scope of the invention.

The present invention also relates to processes for the preparation of a compound of general formula (I), as defined above, their prodrugs, and pharmaceutically acceptable salts, according to the following methods (Method A and Method B), that can be carried out according to methods well known to a person skilled in the art. Some of the processes which can be used are described below and reported in Schemes and should not be viewed as limiting the scope of the synthetic methods available for the preparation of the compounds of the invention. The following processes are given for representative purposes. Depending on the nature of the compounds of the formula (I) to be obtained, the methodologies presented may be adapted by a person skilled in the art by selecting the appropriate starting materials, in which the nature of the substituents R, $R_1$, $R_2$ and $R_3$ may be modified.

It is therefore an object of the invention a process for the preparation of compound (Ia), corresponding to the general formula (I) wherein A is R, the process comprising:

(a) reacting a compound of formula (II) with an acylating agent to give a compound of formula (III),

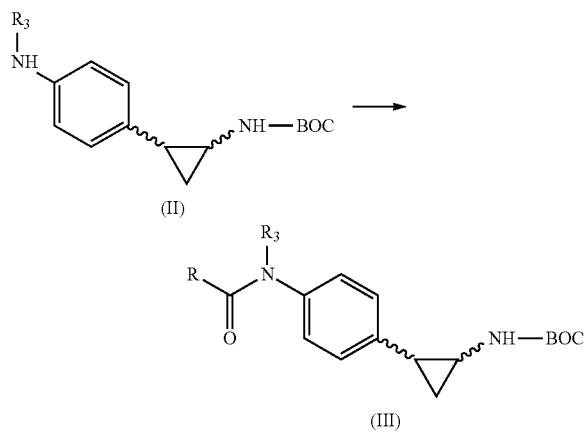

wherein R, R₃ are as defined above and Boc is the tert-butyloxycarbonyl protecting group;

(b) optionally converting the compound of formula (III) obtained in a) into another compound comprised in the formula (III), removing the Boc protecting group from the compound of formula (III) to obtain the compound of formula (Ia):

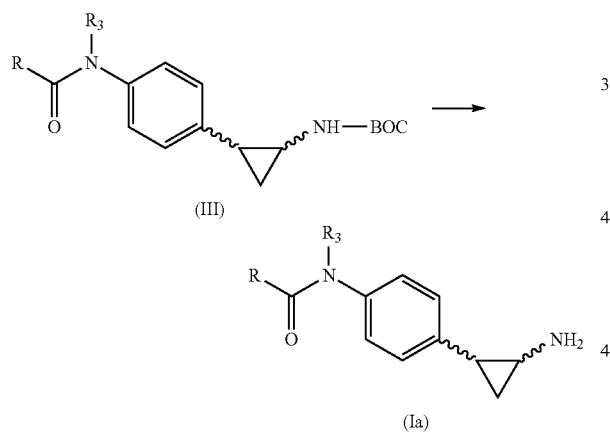

According to step (a) of the process (Method A), the reaction of a compound of formula (II) with an acylating agent to give the compound of formula (III) can be accomplished with different methods well known to a person skilled in the art. As an example, a compound of formula (II) can be treated with the appropriate acylating agent, such as acyl chloride, in the presence of a base to furnish the Boc-protected compound of formula (III). The reaction is carried out in a suitable solvent such as polar aprotic solvents, for instance, dichloromethane, tetrahydrofuran, 1,4-dioxane, N,N'-dimethylformamide, or mixtures thereof, in the presence of a proton scavenger, such as triethylamine, N,N-diisopropylethylamine, piperidine, N,N-dimethylaniline, or pyridine, at a temperature ranging from room temperature to the reflux temperature of the solvent. Preferably, step (a) is carried out by reaction of a compound of formula (II) with acyl chloride in the presence of an amine, such as trietylamine, in dichloromethane at room temperature. Optionally, a compound of formula (III) may be converted into another compound of formula (III), before the deprotection of the Boc group. For instance, the aniline NH can be alkylated by treatment with alkyl halide in basic medium according to standard methods well known to a person skilled in the art. Cleavage of the Boc group from the compound of formula (III) according to standard methods yielded the final compounds (Ia). The deprotection of the Boc group is described in "Protective Groups in Organic Chemistry" 3rd edition, T. W. Greene and P. G. M. Wuts, Wiley-Interscience (1999) and "Protecting Groups", P. J. Kocienski, Georg Thieme Verlag (1994). For example, step (b) is carried out through the addition of an acid, such as HCl or trifluoroacetic acid, in a suitable solvent such as polar aprotic solvents, for instance, dichloromethane, tetrahydrofuran, 1,4-dioxane, N,N'-dimethylformamide, or mixtures thereof, at a temperature ranging from about 0° C. to reflux.

The compounds of formula (Ia) can be modified into other compounds comprised in the formula (Ia) via any synthetic means known in the arts and/or can be converted into a pharmaceutically acceptable salt and/or the salt thereof can be converted into the free compound of formula (Ia).

In another embodiment, the invention provides a process for the preparation of a compound (Ib) corresponding to the general formula (I) wherein A is CH(R₁)—NH—CO—R₂, the process comprising:

(a) reacting a compound of formula (II) with an acylating agent to give a compound of formula (IV)

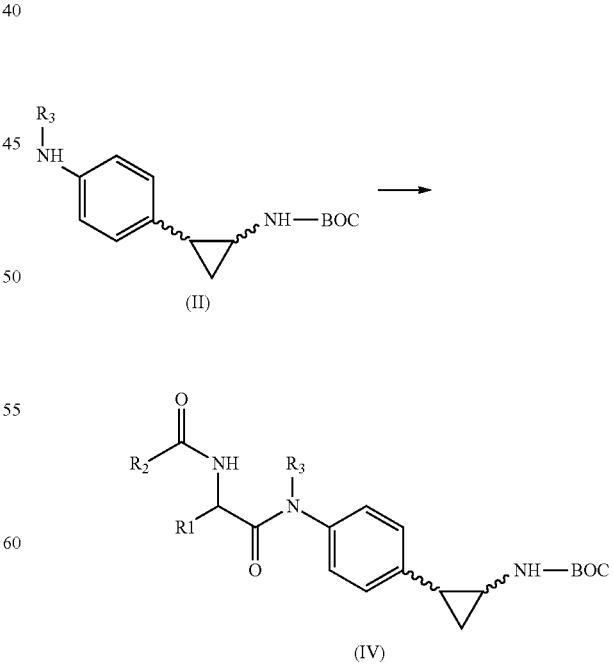

wherein R₁, R₂, R₃ and Boc are as defined above;

(b) optionally converting the compound of formula (IV) obtained in a) into another compound of formula (IV), removing the Boc protecting group from the compound of formula (IV) to obtain a compound of formula (Ib):

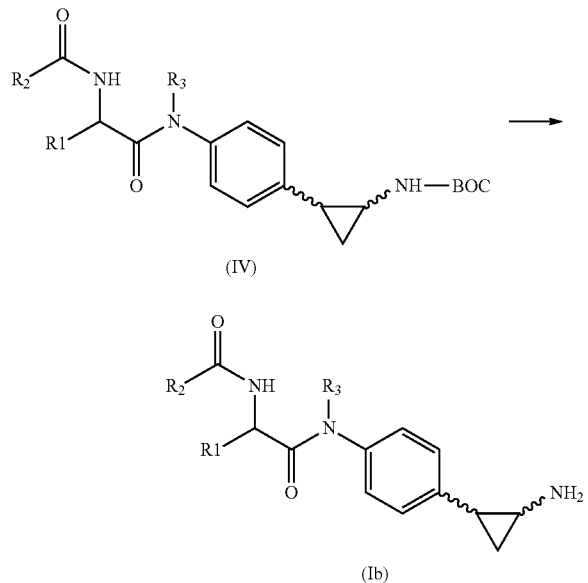

According to step (a) of the process (Method B), the reaction of a compound of formula (II) with an acylating agent to give the compound of formula (IV) can be accomplished with different methods well known to a person skilled in the art. As an example, a compound of formula (II) can be treated with the appropriate acylating agent, such as Z-protected aminoacid, and a base, optionally in the presence of a coupling reagent, such as (benzotriazol-1-yloxy)tris(dimethylamino)-phosphonium hexafluorophosphate (BOP-reagent), N,N-carbonyldiimidazole, or 1-ethyl-3-(3-dimethylaminopropyl) carbodiimide hydrochloride, to furnish the Boc-protected compound of formula (IV). The reaction is carried out in suitable solvents, such as polar aprotic solvents, for instance, dichloromethane, tetrahydrofuran, 1,4-dioxane, N,N'-dimethylformamide, or mixtures thereof, in the presence of a proton scavenger, such as triethylamine, N,N-diisopropylethylamine, piperidine, N,N-dimethylaniline, or pyridine, at a temperature ranging from room temperature to the reflux temperature of the solvent. Preferably, step (a) is carried out by reaction of a compound of formula (II) with a Z-protected aminoacid in the presence of an amine, such as trietylamine, in N,N-dimethylformamide at room temperature. Optionally, a compound of formula (IV) may be converted into another compound of formula (IV) before the deprotection of the Boc group. For instance, the aniline NH can be alkylated by treatment with alkyl halide in basic medium according to standard methods well known to a person skilled in the art. Further cleavage of the Boc group of the compound of formula (IV) by working as described above yielded the final compounds (Ib).

The compounds of formula (Ib) can be modified into other compounds comprised in the formula (Ib) via any synthetic means known in the arts and/or can be converted into a pharmaceutically acceptable salt and/or the salt thereof can be converted into the free compound of formula (Ib).

The acylating agent or the Z-protected aminoacid above are commercially available compounds or can be easily obtained from known compounds according to standard procedures known by those skilled in the art. In case the acylating agent or the Z-protected aminoacid bears reactive groups like hydroxyl, carboxyl, thiol or amino groups, they may need to be protected by protecting groups such as t-butoxycarbonyl, benzyl, benzyloxycarbonyl, methyl, trimethylsilyl and similar and, at a certain step of the synthesis, deprotected to obtain again the free reactive group. The deprotected group may be further reacted, i.e. alkylated, acylated, sulphonylated or similar. The protection and deprotection of functional groups is described in "Protective Groups in Organic Chemistry" 3rd edition, T. W. Greene and P. G. M. Wuts, Wiley-lnterscience (1999) and "Protecting Groups", P. J. Kocienski, Georg Thieme Verlag (1994).

It is clear to the person skilled in the art that if a compound of formula (I), prepared according to the above processes (Method A or Method B), is obtained as an admixture of isomers, their separation into the single isomers of formula (I), carried out according to conventional techniques, is still within the scope of the present invention.

As it will be appreciated by the person skilled in the art, when, during the syntheses of compounds of formula (I) certain functional groups could give rise to unwanted side reactions, these groups need to be properly protected according to conventional techniques. Likewise, the conversion of these latter into the corresponding deprotected compounds may be carried out according to procedures well known to the person skilled in the art.

The starting materials of formula (II) can be obtained from known compounds commercially available according to standard procedures available in the literature and well known to the person skilled in the art. The compounds of formula (II), can be easily obtained following in part reported procedures (*J Am Chem Soc*, 80: 4015-4018, 1958; *J Org Chem*, 27: 733-736, 1962; *Bioorg Med Chem Lett*, 16: 1840-1845, 2006). In particular, ethyl 2-(4-nitrophenyl)cyclopropyl-1carboxylate was obtained as a mixture of cis and trans by coupling of commercially available 4-nitrostyrene with ethyl diazoacetate (EDA), in the presence of copper (I) chloride (CuCl) in dry CHCl$_3$ (Scheme 1). The two isomers can be isolated by using known procedures for the separation of compounds, for example by chromatographic separation, recrystallization techniques, as well as other methods well known to the person skilled in the art. Alkaline hydrolysis of the ethyl ester furnished the corresponding carboxylic acids, which were in turn converted into the related t-butoxy carbamates through reaction with trietylamine, diphenylphosphoryl azide, t-butanol, and di-t-butyldicarbonate in dry benzene. Reduction of the nitro group of these last compounds with sodium hypophosphite, palladium on carbon, and potassium carbonate gave the compounds of formula (II).

Scheme 1:

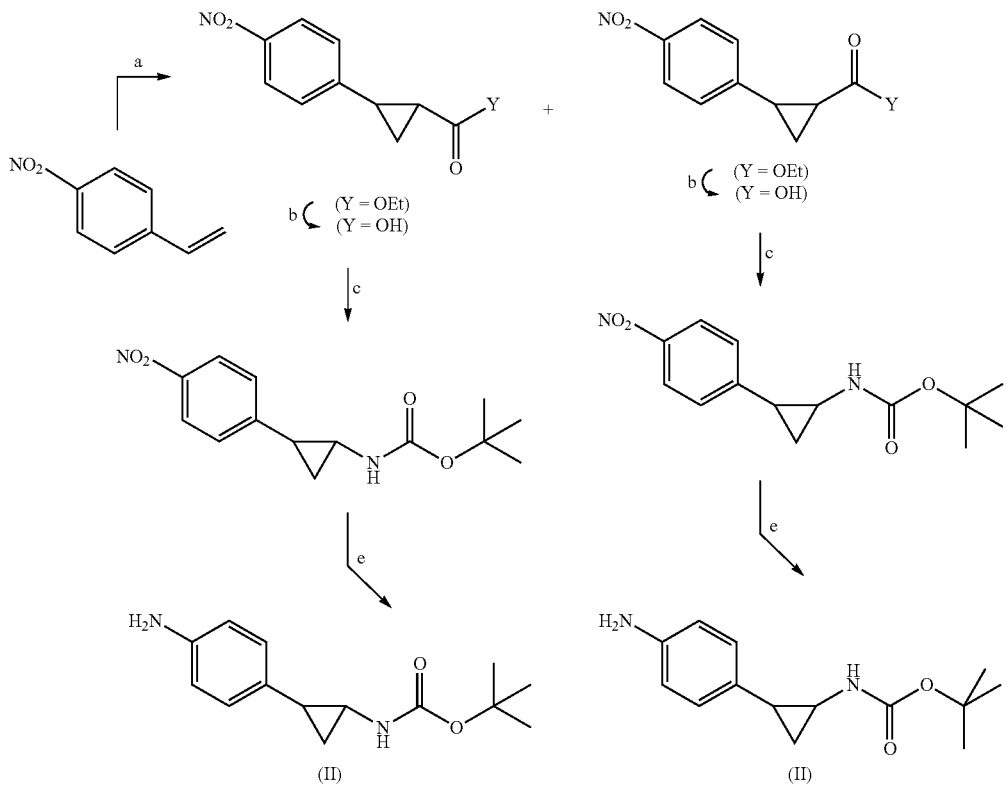

Reagents and conditions:
a) EDA, CuCl, dry CHCl₃, 60° C., N₂ atmosphere; b) 2 N KOH, EtOH, rt; c) 1) DPPA, Et₃N, dry t-BuOH, dry benzene, 80° C., N₂ atmosphere; 2) Boc₂O, dry benzene, 80° C., N₂ atmosphere; e) 2N K₂CO₃, NaH₂PO₂, Pd/C, THF, 60° C., N₂ atmosphere.

The compounds of the present invention were found to be effective LSD1 and LSD2 inhibitors and exhibit anti-tumor activity on leukemic cells when taken alone, and synergistic activities with anti-leukemia drugs when given in combination.

It is an object of the present invention a compound of formula I being an inhibitor of LSD1 and/or LSD2 histone demethylase.

Preferably, the compound of the invention is for use in therapy or as pro-apoptotic agent, still preferably the compound is for use as a medicament for the prevention and/or treatment of diseases characterized by deregulation of gene transcription, cell differentiation and proliferation.

In a preferred embodiment, the compound of the invention is for use as an anti-tumoral agent.

In a further preferred embodiment, the compound is for use as an anti-viral agent.

It is an object of the invention a method for preventing and/or treating diseases and conditions associated with the activity of histone demethylase LSD1 and/or LSD2, in particular tumors, viral infections, by administering to a mammal in need of such treatment a therapeutically effective amount of a compound of general formula (I) as defined above.

Preferably, the tumor is selected from: neuroblastoma, prostate cancer, breast cancer, acute myeloid leukemia, T-lineage acute lymphoblastic leukemia, bladder cancer, lung cancer and colorectal cancer.

Still preferably, the viral infection is caused by Herpes Simplex Virus.

It is an object of the invention a pharmaceutical composition comprising one or more compounds of general formula (I), as defined above, alone or in combination with other active compounds, and at least one pharmaceutically acceptable excipient.

Preferably, the pharmaceutical composition comprises an effective amount of the compound of the invention formulated in unit dosage form.

The term "excipient" herein means any substance, not itself a therapeutic agent, used as a carrier or vehicle for delivery of a therapeutic agent to a subject or added to a pharmaceutical composition to improve its handling or storage properties or to permit or facilitate formation of a dose unit of the composition into a discrete article such as a tablet, capsule, pill, powder, granule, pellet, lozenge, pastille, elixir, syrup, solution, suspension, emulsion, drop, lotion, spray, tincture, cream, ointment, gel, unguent, suppository and transdermal devices for oral, enteral, parenteral or topical administrations.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

A person skilled in the art is aware of a whole variety of such excipients suitable to formulate a pharmaceutical composition. Suitable pharmaceutically acceptable excipients are well known to those skilled in the art. Excipients include, by way of illustration and not limitation, diluents, solubilizers, fillers, agglutinants, disintegrants, disintegration inhibitors, absorption accelerators, adjuvant, binders, carriers, suspensing/dispersing agents, film formers/coatings, adhesives, anti-adherents, wetting agents, lubricants, glidants, preservatives, sorbents, buffering agents, surface active agents, substances added to mask or counteract a disagreeable taste or odor, flavorings, colorants, fragrances, aromatising agents, sweeteners, substances added to improve appearance of the composition, and the like. The choice of excipient will to a large extent depend on factors such as the particular mode of administration, the effect of the excipient on solubility and stability, and the nature of the dosage form.

The pharmaceutical compositions of the present invention can be administered by a variety of routes including oral, parenteral, intravenous, by infusion, subcutaneous, intramuscular, intraperitoneal, transmucosal (including buccal, sublingual, nasal, transurethral and rectal), topical, transdermal, by inhalation, ocular routes (including ocular implants, reservoir implants and injectable therapies such as intravitreal administration), permucous or percutaneous or using any other route of administration.

They will thus be presented in the form of solids or liquids, injectable solutions or suspensions or multi-dose bottles, in the form tablets, plain or coated tablets, sugar or film coated tablets, capsules, wafer capsules, gel capsules, pills, cachets, sachets, powders, granules, caplets, lozenges, bolus, dragees, electuary, past, suppositories or rectal capsules, syrups, elixirs, emulsions, solutions, suspensions, creams, ointments, liniments, lotions, drops, sprays, patches, for percutaneous use in a polar solvent, or for permucous use.

For example, the solid oral forms may contain, together with the active compound, diluents, e.g., alkaline-earth metal carbonates, magnesium phosphate, lactose, dextrose, saccharose, sucrose, cellulose, microcrystalline cellulose derivatives, starches, corn starch or potato starch, modified starches and the like; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycols, a polyoxyethylene sorbitan fatty acid ester surfactants, salicylates or lecithin.

The inhalation aerosols may contain, together with the active compound, propellant gas, such as hydrofluoroalkanes. The propellant-driven formulations may also contain other ingredients such as co-solvents, stabilizers and optionally other excipients. The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers.

The above described components for pharmaceutical composition administered are merely representative. Further materials as well as processing techniques and the like are set out in Part 5 of Remington's Pharmaceutical Sciences, $20^{th}$ Edition, 2000, Merck Publishing Company, Easton, Pa., which is incorporated herein by reference. Compound of this invention of formula (I) can also be administered in sustained release forms or from sustained release drug delivery systems. A description of representative sustained release materials can also be found in the incorporated materials in Remington's Pharmaceutical Sciences.

The pharmaceutical compositions containing the compounds of the invention are usually prepared following conventional methods and are administered in a suitable pharmaceutical form.

Solid oral compositions can be prepared by conventional mixing, filling or compression. It is possible to repeat the mixing operations in order to disperse the active agent in compositions containing high amounts of fillers. These operations are conventional.

Liquid oral preparations can be formulated e.g. as aqueous or oily suspensions or solutions, emulsions, syrups or elixir, or can be presented as freeze dried product to be regenerated by addition of water or a suitable vehicle before use. Said liquid preparations can contain conventional additives such as suspending agents, e.g. sorbitol, syrup, methylcellulose, gelatine, hydroxyethylcellulose, carboxymethylcellulose, alluminium stearate gel or hydrogenated edible fats, emulsifying agents, e.g. lecithin, sorbitan monooleate, or acacia; non-aqueous vehicles (which may include edible oils), e.g. almond oil, fractionated coconut oil, oily esters such as glycerin esters, propylene glycol, or ethyl alcohol; preservatives, e.g. methyl or propyl p-hydroxybenzoate or sorbic acid and, if desired, conventional flavours and dyes.

For parenteral administration, it is possible to prepare fluid dosage units, containing the compound and a sterile vehicle. The compound, depending on the chosen vehicle and concentration, can be suspended or dissolved. Parenteral solutions are normally prepared by dissolving the compound in a vehicle, sterilizing by filtration, filling suitable vials and sealing. Advantageously it is also possible to dissolve in the vehicle suitable adjuvants such as local anesthetic, preservatives and buffering agents. In order to increase stability, the composition can be frozen after filling the vial and removing water under vacuum. Parenteral suspensions are prepared substantially in the same way, with the difference that the compound can be suspended rather than dissolved in the vehicle, and they can be sterilized by treatment with ethylene oxide before being suspended in the sterile vehicle. Advantageously, it is possible to include a surfactant or a wetting agent in the composition with the aim of easing the uniform distribution of the compound of the invention.

The compounds of the invention can also be administered topically. Topical formulations may comprise, for example, an ointment, cream, gel, lotion, solution, paste or the like, and/or may be prepared so as to contain liposomes, micelles, and/or microspheres. Ointments, as it is well known in the art of pharmaceutical formulation, are semisolid preparations that are typically based on petrolatum or other petroleum derivatives. Examples of ointments include oleaginous ointment bases, for example, vegetable oils, fats obtained from animals, and semisolid hydrocarbons obtained from petroleum, emulsifiable ointment bases, for example, hydroxystearin sulfate, anhydrous lanolin and hydrophilic petrolatum, emulsion ointment bases, for example, cetyl alcohol, glyceryl monostearate, lanolin and stearic acid and water-soluble ointment bases prepared from polyethylene glycols of varying molecular weight. Creams, as also well known to those skilled in the art, are viscous liquids or semisolid emulsions, and contain an oil phase, an emulsifier and an aqueous phase. The oil phase is generally comprised of petrolatum and a fatty alcohol such as cetyl or stearyl alcohol. The aqueous phase usually contains a humectant. The emulsifier in a cream formulation is chosen among non-ionic, anionic, cationic or amphoteric surfactants. Single-phase gels contain organic macromolecules distributed substantially uniformly throughout the carrier liquid, which is typically aqueous, but also, preferably, contain an alcohol and, optionally, an oil. Preferred gelling agents are crosslinked acrylic acid polymers (such as "carbomer" polymers, e. g., carboxypolyalkylenes that may be obtained commercially under the Carbopol trademark). Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. For the preparation of uniform gels, dispersing agents such as alcohol or glycerin can be added, or the gelling agent can be dispersed by trituration, mechanical mixing, and/or stirring.

The compounds of the invention may also be administered via transdermal release. Typical transdermal formulations include conventional aqueous and non aqueous vectors, such as creams, oils, lotions or pastes or can be provided as membranes or medicated plasters. In an embodiment, a compound of the invention is dispersed in a pressure-sensible plaster adhering to the skin. This formulation allows the compound to be spread from the plaster to the patient through the skin. In order to obtain a sustained drug release through the cutis, natural rubber and silicon can be used as pressure-sensitive adhesives.

The compounds of formula (I) of the present invention, suitable for administration to a mammal, e.g., to humans, can be administered as the sole active agent or in combination with other pharmaceutical active ingredients by the usual routes and the dosage level depends on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

For example, a suitable dosage adopted for oral administration of a compound of formula (I) may range from about 30 to 500 mg per dose, from 1 to 5 times daily. In general lower doses will be administered when a parental route is employed.

Thus, for example, for intravenous administration a dose in the range, for example, 0.5 mg to 30 mg per kg body weight will be generally used.

The compounds of the invention can be administered in a variety of dosage forms, e.g., orally, in the form of tablets, sugar or film coated tablets, capsules, cachets, as a powder or granules; as a syrups, emulsions, solution or a suspension in an aqueous or non-aqueous liquid, as an oil-in-water liquid emulsion or a water-in-oil liquid emulsion, as a bolus, electuary or paste; rectally, in the form of suppositories; parenterally, e.g., intramuscularly, or through intravenous injection or infusion. Preferably, the compounds of general formula (I) alone or combined with other active ingredients may be administered for the prevention and/or treatment of any disease wherein histone demethylases LSD1 and LSD2 inhibition is required. Said diseases include tumors, viral infections.

EXAMPLES

The present invention will be now described by means of the following non limiting examples, referring to the following figure.

FIG. 1. Biological evaluation of 6e. (A) 6e synergizes with retinoic acid (RA) in inhibiting cell growth. NB4 cells were treated with increasing concentrations of retinoic acid (10 nM, 100 nM and 1 μM) in the absence or in the presence of 6e (2 μM). At the indicated time points, cells were counted by Tripan blue exclusion. NT, untreated cells (vehicle only). (B) 6e synergizes with retinoic acid (RA) in inducing differentiation in NB4 cells. NB4 cells were treated with retinoic acid (100 nM) or vehicle (NT), in the absence or in the presence of 6e (2 μM). After 7 days cells were cyto-spun on glass slides and stained (May Grunwald-Giemsa).

Figure 2:
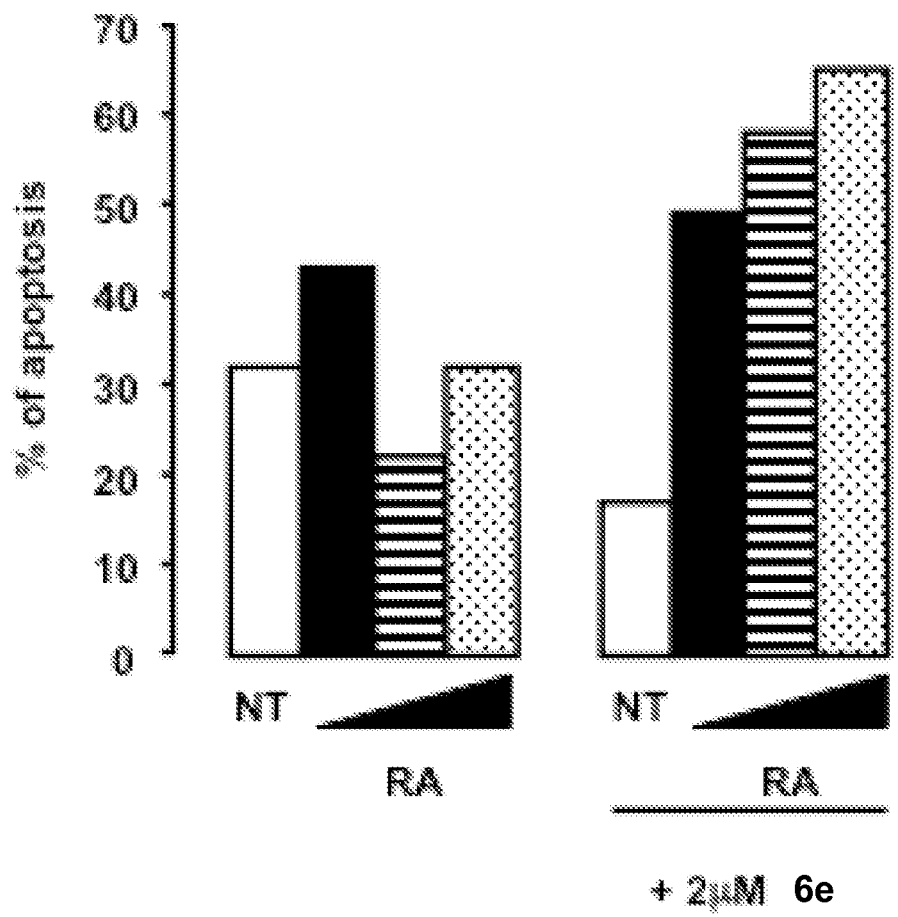

FIG. 2. 6e synergizes with retinoic acid (RA) in inducing apoptosis in NB4 cells. NB4 cells were treated with increasing concentrations of retinoic acid (10 nM, 100 nM and 1 μM) or vehicle (NT), in the absence or in the presence of 6e (2 μM). Apoptosis was measured by propidium iodide staining of permeabilized cells after 7 days. A representative experiment is shown.

1. CHEMICAL SYNTHESIS

Methods

Unless otherwise indicated, all the starting reagents were found to be commercially available or easily obtainable following literature procedures, and were used without any purification. All solvents were reagent grade and, when necessary, were purified and dried by standard methods. Concentration of solutions after reactions and extractions involved the use of a rotary evaporator operating at reduced pressure of ca. 20 Torr. Organic solutions were dried over anhydrous sodium sulfate. Analytical results are within ±0.40% of the theoretical values.

TLC was performed on aluminum-backed silica gel plates (Merck DC, Alufolien Kieselgel 60 F254) with spots visualized by UV light.

The $^1$H NMR and $^{13}$C NMR spectra were acquired with a Bruker 400 MHz. The chemical shifts are expressed in parts per million (ppm, δ units). The coupling constants are expressed in Hertz (Hz) and the splitting patterns are described as s (singlet), bs (broad singlet), d (doublet), t (triplet), q (quartet), quint (quintet), m (multiplet).

EIMS spectra were recorded with a Fisons Trio 1000 spectrometer; only molecular ions ($M^+$) and base peaks are given.

Melting points were determined on a Buchi 530 melting point apparatus and are uncorrected.

Example 1

Preparation of trans and cis tert-Butyl 2-(4-Nitrophenyl)cyclopropyl Carbamates: trans tert-Butyl 2-(4-Nitrophenyl)cyclopropyl Carbamate

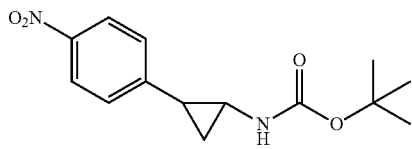 [SMILES: CC(C)(C)OC(=O)NC1CC1c1ccc([N+](=O)[O-])cc1]

A solution of trans 2-(4-nitrophenyl)cyclopropyl-1-carboxylic acid (5.3 mmol, 1.1 g) in dry benzene (20 mL), triethylamine (6.4 mmol, 0.9 mL), diphenylphosphoryl azide (5.8 mmol; 1.2 mL) and tert-butanol (53 mmol, 5 mL) was stirred at 80° C. under $N_2$ atmosphere for 16 h. Afterwards, di-tert-butyldicarbonate (8 mmol, 1.7 g) was added, and the reaction was stirred at 80° C. for further 2 h. The solvent was removed under vacuum and the residue was chromatographed by silica gel eluting with ethyl acetate/n-hexane 1/3 to isolate the pure trans tert-butyl 2-(4-nitrophenyl)cyclopropyl carbamate as a pale yellow solid.

$^1$H NMR (CDCl3, 400 MHz, δ; ppm) δ 1.29-1.33 (m, 2H, $CH_2$ cyclopropane), 1.46 (s, 9H, $C(CH_3)_3$), 2.15-2.17 (m, 1H, PhCH), 2.80-2.82 (m, 1H, CHNH), 4.93 (bs, 1H, NHCO), 7.26-7.28 (d, 2H, aromatic protons), 8.13-8.15 (d, 2H, aromatic protons); $^{13}$C NMR (DMSO-$d_6$, 400 MHz, δ; ppm) δ 14.40, 22.80, 28.40 (3C), 32.60, 79.50, 123.30 (2C), 125.90 (2C), 144.30, 147.80, 155.60; MS (ESI) m/z: 278.13 [M]$^+$; m.p.=153-155° C.

Example 2

Preparation of trans and cis tert-Butyl 2-(4-Aminophenyl)cyclopropyl Carbamates: trans tert-Butyl 2-(4-Aminophenyl)cyclopropyl Carbamate

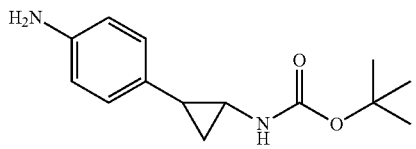

A mixture of trans tert-butyl 2-(4-nitrophenyl)cyclopropyl carbamate (2.88 mmol; 0.8 g), potassium carbonate (2.04 mmol; 0.28 g), 10% palladium on carbon (0.016 g) in tetrahydrofuran (3.88 mL) and water (3.8 mL) was degassed for 5 min, then a sodium hypophosphite solution (10.96 mmol, 1.16 g) in water (2.32 mL) was added dropwise under vigorous stirring. The resulting mixture was stirred at 60° C. for 5 h. The solvent was removed and the residue poured in water (100 mL) and extracted with diethyl ether (3×50 mL). The organic layers were washed with saturated sodium chloride solution (3×50 mL), dried with anhydrous sodium sulfate and concentrated. The residue was chromatographed on silica gel eluting with ethyl acetate/n-hexane 1/2 to afford tert-butyl 1-(4-aminophenyl)propan-2-yl carbamate as first eluate followed by trans tert-butyl 2-(4-aminophenyl)cyclopropyl carbamate, both as yellow oils.

$^1$H NMR (CDCl$_3$, 400 MHz, δ; ppm) δ 1.06-1.10 (m, 2H, $CH_2$ cyclopropane), 1.47 (s, 9H, $C(CH_3)_3$), 1.95-1.97 (m, 1H, PhCH), 2.63-2.65 (m, 1H, CHNH), 3.58 (bs, 2H, $NH_2$), 4.71 (bs, 1H, NHCO), 6.61-6.63 (d, 2H, benzene protons), 6.96-6.98 (d, 2H, benzene protons); $^{13}$C NMR (CDCl$_3$, 400 MHz, δ; ppm) δ 14.40, 22.80, 28.40 (3C), 32.60, 79.50, 114.60 (2C), 125.80 (2C), 131.70, 144.80, 155.60; MS (ESI) m/z: 248.15 [M]$^+$

Example 3

Preparation of trans tert-butyl 2-(4-aroyl (or arylacetyl or benzyloxycarbonyl)aminophenyl)cyclopropyl carbamates (1a-h)

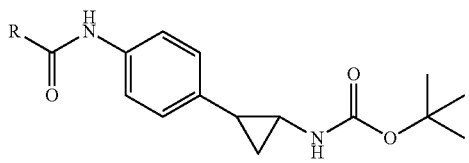

trans tert-butyl 2-(4-benzoylaminophenyl)cyclopropyl carbamate (1b)

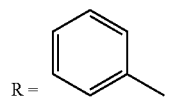

R =

Triethylamine (0.72 mmol, 0.1 mL) and benzoyl chloride (0.6 mmol, 0.09 mL) were added dropwise, with ice-bath external cooling, to a solution of trans tert-butyl 2-(4-aminophenyl)cyclopropyl carbamate (0.6 mmol, 0.150 g) in dry dichloromethane (5 mL). The resulting mixture was stirred for 1 h, then water (50 mL) was added, the organic layer was separated and the aqueous layer extracted with dichloromethane (2×30 mL). The organic phase was washed with saturated sodium chloride solution (3×50 mL), dried with anhydrous sodium sulfate and concentrated. The residue was purified by chromatographic column on silica gel eluting with ethyl acetate/n-hexane 1/3 to obtain pure compound 1b as a white solid.

$^1$H NMR (CDCl$_3$, 400 MHz, δ; ppm) δ 1.12-1.15 (m, 2H, $CH_2$ cyclopropane), 1.47 (s, 9H, $C(CH_3)_3$), 2.00-2.02 (m, 1H, PhCH), 2.70-2.72 (m, 1H, CHNH), 4.88 (bs, 1H, CHNHCO), 7.14-7.16 (d, 2H, aromatic protons), 7.51-7.59 (m, 3H, aromatic protons), 7.70-7.72 (d, 2H, aromatic protons), 7.94-7.96 (d, 2H, aromatic protons), 10.25 (bs, 1H, PhNHCO); $^{13}$C NMR (CDCl$_3$, 400 MHz, δ; ppm) δ 14.40, 22.80, 28.40 (3C), 32.60, 79.50, 121.0 (2C), 125.20 (2C), 127.50 (2C), 128.80 (2C), 132.10, 134.20, 134.30, 137.30, 155.60, 164.70; MS (ESI) m/z: 352.18 [M]$^+$; m.p.=172-174° C.

The following compounds (Table 2) were prepared according to the procedure described above, with suitable reagents:

TABLE 2

| Compound | R | Melting Point (° C.) | Recrystallization Solvent | Yield (%) |
|---|---|---|---|---|
| 1a | benzyl methyl ether group (PhCH₂O–) | 114-116 | cyclohexane/benzene | 82 |
| 1c | 1-naphthylmethyl | 151-153 | benzene/acetonitrile | 73 |
| 1d | 2-naphthylmethyl | 189-191 | acetonitrile | 69 |
| 1e | 4-biphenylmethyl | 218-220 | acetonitrile/methanol | 75 |
| 1f | phenylethyl | 177-179 | benzene/acetonitrile | 71 |
| 1g | 1-naphthylethyl | 165-167 | benzene/acetonitrile | 73 |
| 1h | 2-naphthylethyl | 198-200 | acetonitrile/methanol | 76 |

Example 4

Preparation of: trans tert-butyl 2-[4-(N-benzyloxycarbonylaminoacyl)aminophenyl]cyclopropyl carbamates (2a-m); trans tert-butyl 2-[4-(N-4-bromobenzyloxycarbonylphenylalanyl)phenyl]cyclopropyl carbamate (3); cis tert-butyl 2-[4-(N-benzyloxycarbonylphenylalanyl)phenyl]cyclopropyl carbamate (4)

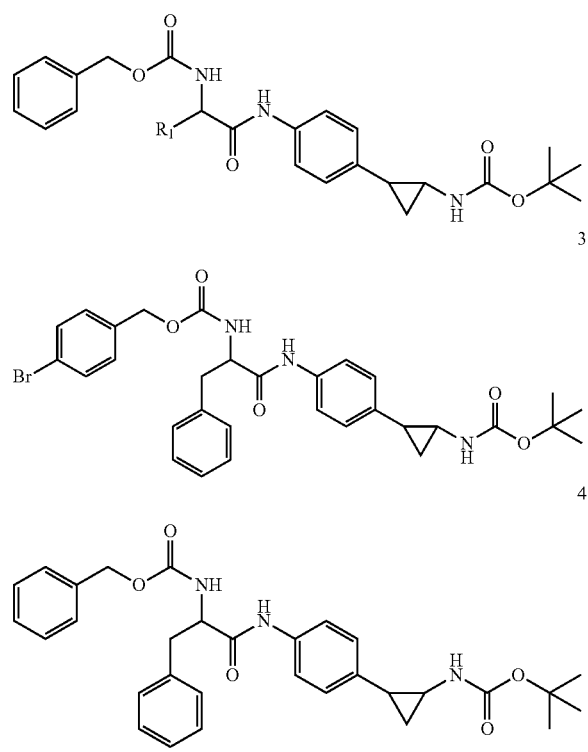

trans tert-butyl 2-[4-(N-benzyloxycarbonylphenylalanyl)phenyl]cyclopropyl carbamate (2e)

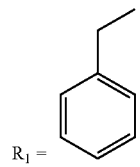

Triethylamine (2.96 mmol, 0.41 mL) and BOP-reagent (0.89 mmol, 0.39 g) were added under $N_2$ atmosphere to a solution of N-benzyloxycarbonylphenylalanine (0.74 mmol, 0.22 g) in dry dimethylformamide (2 mL), and the mixture was stirred for 0.5 h. trans tert-Butyl 2-(4-aminophenyl)cyclopropyl carbamate (0.81 mmol, 0.2 g) was added under $N_2$ atmosphere and the mixture was stirred overnight. The reaction was poured into water (50 mL) and extracted with ethyl acetate (3×30 mL). The organic layers were washed with saturated sodium chloride solution (3×50 mL), dried with anhydrous sodium sulfate and concentrated. The residue was purified by chromatographic column on silica gel eluting with ethyl acetate/chloroform 1/5 to afford the pure compound 2e as a white solid.

$^1$H NMR (CDCl$_3$, 400 MHz, δ; ppm) δ 0.87-0.89 (m, 1H, CHH cyclopropane), 1.05-1.07 (m, 1H, CHH cyclopropane), 1.47 (s, 9H, C(CH$_3$)$_3$), 1.99-2.01 (m, 1H, PhCH), 2.67-2.69 (m, 1H, CHNH), 3.08-3.13 (m, 2H, PhCH$_2$CH), 4.54-4.56 (m, 1H, PhCH$_2$CH), 4.89 (bs, 1H, NHCOOC(CH$_3$)$_3$), 5.10 (s, 2H, PhCH$_2$OCONH), 5.60 (bs, 1H, NHCOOBn), 7.03-7.05 (d, 2H, aromatic protons), 7.21-7.34 (m, 12H, aromatic protons), 7.77 (bs, 1H, PhNHCOCH); $^{13}$C NMR (CDCl$_3$, 400 MHz, δ; ppm) δ 14.40, 22.80, 28.40 (3C), 32.60, 37.30, 58.40, 66.80, 79.50, 121.0 (2C), 125.20 (2C), 125.90, 127.10 (2C), 127.60, 127.70 (2C), 128.60 (2C), 128.90 (2C), 134.90, 136.10, 136.60, 137.30, 155.60, 155.90, 172.70; MS (ESI) m/z: 529.26 [M]$^+$; m.p.=161-163° C.

The following compounds (Table 3) were prepared according to the procedure described above, with suitable reagents:

TABLE 3

| Compound | R$_1$ | Melting Point (° C.) | Recrystallization Solvent | Yield (%) |
|---|---|---|---|---|
| 2a | | oil | — | 62 |
| 2b | | oil | — | 89 |

TABLE 3-continued
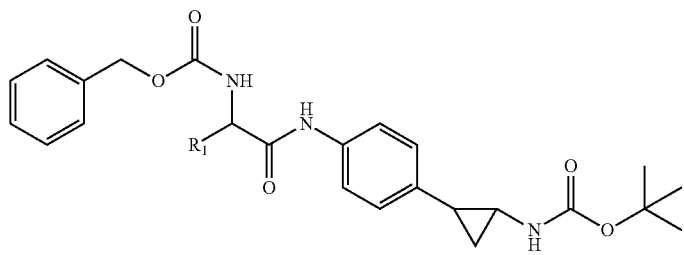
| Compound | R₁ | Melting Point (° C.) | Recrystallization Solvent | Yield (%) |
|---|---|---|---|---|
| 2c | cyclohexylmethyl | oil | — | 50 |
| 2d | benzyl | 66-68 | cyclohexane | 68 |
| 2f | 4-bromobenzyl | 155-157 | benzene | 73 |
| 2g | 4-methoxybenzyl | 98-100 | cyclohexane/benzene | 50 |
| 2h | phenethyl | 150-152 | benzene | 77 |
| 2i | diphenylmethyl (with methyl) | 108-110 | cyclohexane/benzene | 73 |
| 2j | 1-naphthylmethyl | 186-188 | acetonitrile | 55 |

TABLE 3-continued

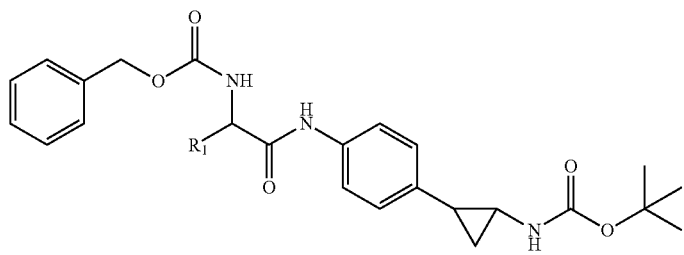

| Compound | R₁ | Melting Point (° C.) | Recrystallization Solvent | Yield (%) |
|---|---|---|---|---|
| 2k | (2-naphthylethyl) | 143-145 | benzene | 60 |
| 2l | (indol-3-ylethyl) | 142-144 | benzene | 67 |
| 2m | (benzothiophen-3-ylethyl) | 115-117 | cyclohexane/benzene | 62 |
| 3 | | 148-150 | benzene | 76 |
| 4 | | 168-170 | benzene/acetonitrile | 83 |

Example 5

Preparation of: trans 2-(4-aroyl (or arylacetyl or benzyloxycarbonyl))aminophenylcyclopropylamine hydrochlorides (5a-h); trans 4-(N-benzyloxycarbonylaminoacyl)aminophenylcyclopropylamines hydrochlorides (6a-m); trans 4-bromobenzyl 1-(4-(2-aminocyclopropyl)phenylamino)-1-oxo-3-phenylpropan-2-ylcarbamate hydrochloride (7); cis benzyl 1-(4-(2-aminocyclopropyl)phenylamino)-1-oxo-3-phenylpropan-2-ylcarbamate hydrochloride (8)

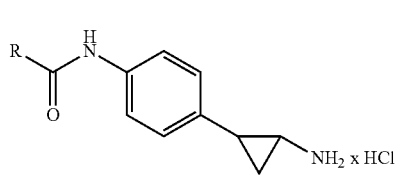

5a-h

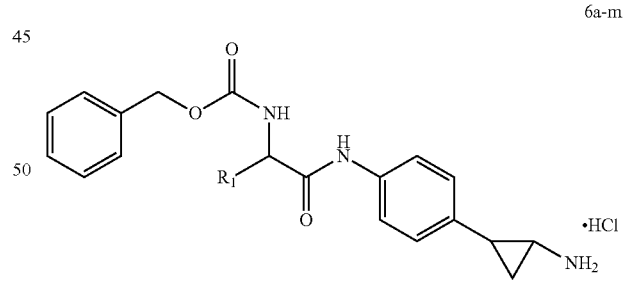

6a-m

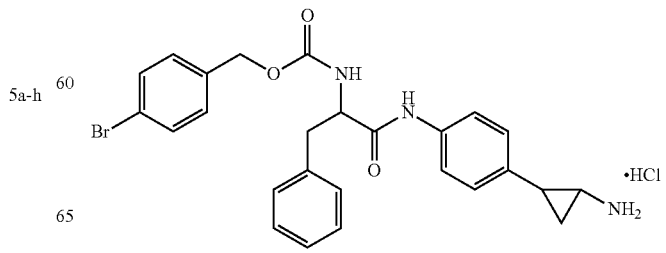

7

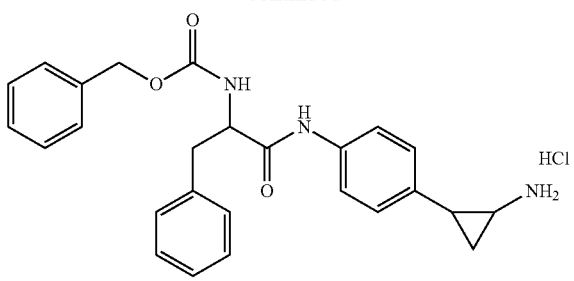

trans benzyl 1-(4-(2-aminocyclopropyl)phenylamino)-4-(1H-indol-3-yl)-1-oxobutan-2-ylcarbamate hydrochloride (6l)

$R_1 =$ 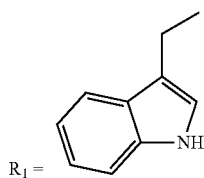

A 6 N HCl aqueous solution (2 mL) was added to a solution of 2l (0.26 mmol, 0.1 g) in tetrahydrofuran (2 mL), and the mixture was stirred for 12 h at room temperature. The precipitated solid was filtered off, washed with diethyl ether (3×10 mL) and dried to give the pure 6l as a colorless solid.

$^1$H NMR (DMSO-$d_6$, 400 MHz, δ; ppm) δ 1.15-1.17 (m, 1H, CHH cyclopropane), 1.34-1.36 (m, 1H, CHH cyclopropane), 2.27-2.29 (m, 1H, PhCH), 2.74-2.76 (m, 1H, CHNH$_3$Cl), 3.02-3.04 (dd, 1H, indole-CHHCH), 3.13-3.15 (dd, 1H, indole-CHHCH), 4.43-4.45 (m, 1H, indole-CH$_2$CH), 4.97 (s, 2H, PhCH$_2$OCONH), 6.98-7.75 (m, 14H, aromatic protons), 8.33 (bs, 3H, NH$_3$Cl), δ 10.16 (bs, 1H, PhNHCO), 10.86 (bs, 1H, indole-NH); $^{13}$C NMR (DMSO-$d_6$, 400 MHz, δ; ppm) δ 14.0, 22.0, 27.80, 28.0, 59.50, 66.80, 109.70, 111.10, 118.80, 119.80, 121.0 (2C), 121.70, 123.0, 125.20 (2C), 127.10 (2C), 127.40, 127.60, 128.90 (2C), 134.90, 136.10, 136.50, 138.90, 155.90, 172.70; MS (ESI) m/z: 504.19 [M]$^+$; m.p.=>250° C.

The following compounds (Table 4 and Table 5) were prepared according to the procedure described above, with suitable reagents:

TABLE 4

| Compound | R | Melting Point (° C.) | Recrystallization Solvent | Yield (%) |
|---|---|---|---|---|
| 5a | benzyl methoxymethyl | 227-229 | acetonitrile/methanol | 80 |
| 5b | tolyl | 210-212 | acetonitrile/methanol | 83 |
| 5c | 1-naphthyl | >250 | methanol | 76 |
| 5d | 2-naphthyl | >250 | methanol | 81 |

TABLE 4-continued
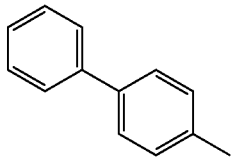
| Compound | R | Melting Point (° C.) | Recrystallization Solvent | Yield (%) |
|---|---|---|---|---|
| 5e | 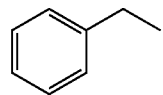 | >250 | methanol | 85 |
| 5f | 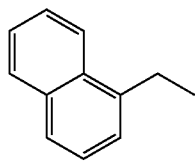 | 180-182 | acetonitrile | 73 |
| 5g | 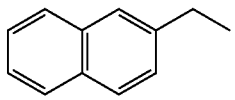 | 240-242 | acetonitrile/methanol | 78 |
| 5h |  | 238-240 | acetonitrile/methanol | 84 |
TABLE 5
| Compound | $R_1$ | Melting Point (° C.) | Recrystallization Solvent | Yield (%) |
|---|---|---|---|---|
| 6a | | 168-170 | benzene/acetonitrile | 75 |
| 6b | | 158-160 | benzene/acetonitrile | 70 |
| 6c | 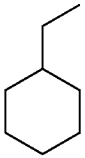 | 120-122 | cyclohexane/benzene | 53 |

TABLE 5-continued

| Compound | R₁ | Melting Point (° C.) | Recrystallization Solvent | Yield (%) |
|---|---|---|---|---|
| 6d | phenyl | 135-137 | cyclohexane/benzene | 68 |
| 6e | benzyl | 220-222 | acetonitrile | 72 |
| 6f | 4-bromobenzyl | 215-217 | acetonitrile/methanol | 79 |
| 6g | 4-methoxybenzyl | 173-175 | benzene/acetonitrile | 57 |
| 6h | phenethyl | 198-200 | acetonitrile | 76 |
| 6i | 1,1-diphenylethyl | 200-202 | acetonitrile | 66 |
| 6j | 1-naphthylmethyl | 160-162 | benzene/acetonitrile | 65 |

TABLE 5-continued

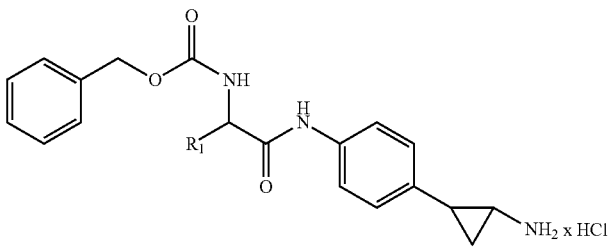

| Compound | $R_1$ | Melting Point (° C.) | Recrystallization Solvent | Yield (%) |
|---|---|---|---|---|
| 6k | (2-naphthylmethyl) | 156-158 | benzene/acetonitrile | 68 |
| 6m | (benzothiophen-3-ylmethyl) | 157-159 | benzene/acetonitrile | 69 |
| 7 | | 220-222 | acetonitrile/methanol | 84 |
| 8 | | 215-217 | acetonitrile/methanol | 77 |

Example 6

Preparation of $N^1$-(4-trans(2-aminocyclopropyl)phenyl)-$N^8$-hydroxyoctanediamide hydrochloride (9)

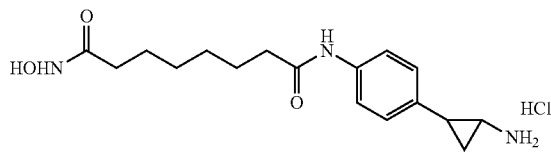

Step a

Synthesis of methyl 8-(4-trans(2-tert-butoxycarbonylaminocyclopropyl)phenylamino)-8-oxooctanoate Triethylamine (0.68 mmol, 0.09 mL) and methyl 8-chloro-8-oxooctanoate (0.564 mmol, 0.08 mL) were added dropwise with ice-bath external cooling to a solution of trans tert-butyl 2-(4-aminophenyl)cyclopropyl carbamate (0.56 mmol, 140 mg) in dry dichloromethane (5 mL). The resulting mixture was stirred for 1 h, then water (50 mL) was added, the organic layer was separated and the aqueous layer extracted with dichloromethane (2×30 mL). The final organic solution was washed with saturated sodium chloride solution (3×50 mL), dried with anhydrous sodium sulfate and concentrated. The residue was purified by chromatographic column on silica gel eluting with ethyl acetate/chloroform 1/2 to obtain the pure compound methyl 8-(4-trans(2-tert-butoxycarbonylaminocyclopropyl)phenylamino)-8-oxooctanoate as a white solid.

$^1$H NMR (CDCl$_3$, 400 MHz, δ; ppm) δ 1.12-1.15 (m, 2H, CH$_2$ cyclopropane), 1.37-1.39 (m, 4H, OCOCH$_2$CH$_2$CH$_2$CH$_2$CH$_2$CH$_2$CON), 1.47 (s, 9H, C(CH$_3$)$_3$), 1.63-1.65 (m, 2H, OCOCH$_2$CH$_2$CH$_2$CH$_2$CH$_2$CH$_2$CON) 1.71-1.73 (m, 2H, OCOCH$_2$CH$_2$CH$_2$CH$_2$CH$_2$CH$_2$CON) 2.00-2.02 (m, 1H, PhCH), 2.30-2.35 (m, 4H, OCOCH$_2$CH$_2$CH$_2$CH$_2$CH$_2$CH$_2$CON), 2.70-2.72 (m, 1H, CHNH), 3.68 (s, 3H, OCH$_3$) 4.88 (bs, 1H, CHNHCO), 7.08-7.10 (d, 2H, aromatic protons), 7.40-7.42 (d, 2H, aromatic protons), 7.28 (bs, 1H, PhNHCO); $^{13}$C NMR (CDCl$_3$, 400 MHz, δ; ppm) δ 14.40, 22.80, 25.00, 25.60, 28.30 (2C), 28.40 (3C), 32.60, 33.60, 38.30, 51.90, 79.50, 121.00 (2C), 125.20 (2C), 134.90, 137.30, 155.60, 173.10, 179.80; MS (ESI) m/z: 418.24 [M]$^+$

Step b

Synthesis of 8-(4-trans(2-tert-butoxycarbonylaminocyclopropyl)phenylamino)-8-oxooctanoic acid A solution of the above methyl 8-(4-trans (2-tert-butoxycarbonylaminocyclopropyl)phenylamino)-8-oxooctanoate (0.53 mmol, 220 mg) and LiOH (1.05 mmol, 44 mg) in tetrahydrofuran/water (5 mL/5 mL) was stirred overnight at room temperature. The reaction was quenched by addition of 2 N HCl until pH=4, then the precipitate was filtered, washed with water (3×30 mL) and dried to obtain the pure 8-4-trans (2-tert-butoxycarbonylaminocyclopropyl)phenylamino)-8-oxooctanoic acid as a white solid.

$^1$H NMR (DMSO-d$_6$, 400 MHz, δ; ppm) δ 0.98-1.00 (m, 1H, CHH cyclopropane), 1.02-1.05 (m, 1H, CHH cyclopropane), 1.24-1.29 (m, 4H, OCOCH$_2$CH$_2$CH$_2$CH$_2$CH$_2$CON), 1.38 (s, 9H, C(CH$_3$)$_3$), 1.48-1.50 (m, 2H, OCOCH$_2$CH$_2$CH$_2$CH$_2$CH$_2$CH$_2$CON), 1.56-1.59 (m, 2H, OCOCH$_2$CH$_2$CH$_2$CH$_2$CH$_2$CH$_2$CON), 1.82-1.84 (m, 1H, PhCH), 2.17-2.19 (m, 2H, OCOCH₂CH₂CH₂CH₂CH₂CON), 2.25-2.27 (m, 2H, OCOCH₂CH₂CH₂CH₂CH₂CON), 2.50-2.52 (m, 1H, CHNH), 6.99-7.01 (d, 2H, benzene protons), 7.20 (bs, 1H, PhNHCO), 7.45-7.47 (d, 2H, benzene protons), 9.76 (bs, 1H, CHNHCO), 12.0 (bs, 1H, COOH); ¹³C NMR (CDCl₃, 400 MHz, δ; ppm) δ 14.40, 22.80, 24.70, 25.60, 28.30 (2C), 28.40 (3C), 32.60, 34.00, 38.30, 79.50, 121.00 (2C), 125.20 (2C), 134.90, 137.30, 155.60, 178.00, 179.80; MS (ESI) m/z: 404.23 [M]⁺.

OCOCH₂CH₂CH₂CH₂CH₂CH₂CON), 2.70-2.72 (m, 1H, PhCH), 3.06-3.05 (m, 1H, CHNH₃Cl), 7.05-7.07 (d, 2H, aromatic protons), 7.51-7.53 (d, 2H, aromatic protons), 8.56 (bs, 3H, NH₃Cl), 9.91 (s, 1H, PhNHCO), 10.09 (s, 1H, CONHOH), 12.0 (bs, 1H, CONHOH); ¹³C NMR (CDCl₃, 400 MHz, δ; ppm) δ 14.00, 22.00, 25.60 (2C), 27.90 (2C), 28.00, 32.50, 38.30, 121.00 (2C), 125.20 (2C), 134.90, 138.90, 169.90, 179.80;

MS (ESI) m/z: 320.19 [M]⁺

Example 7

Synthesis of trans benzyl 1-((4-(2-aminocyclopropyl)phenyl)(methyl)amino)-1-oxo-3-phenylpropan-2-ylcarbamate hydrochloride (12)

Step c

Synthesis of N¹-(4-trans-(2-aminocyclopropyl)phenyl)-N⁸-hydroxyoctanediamide hydrochloride (9)

Ethyl chloroformate (0.384 mmol, 0.04 mL) and triethylamine (0.42 mmol, 0.06 mL) were added to a cooled (0° C.)

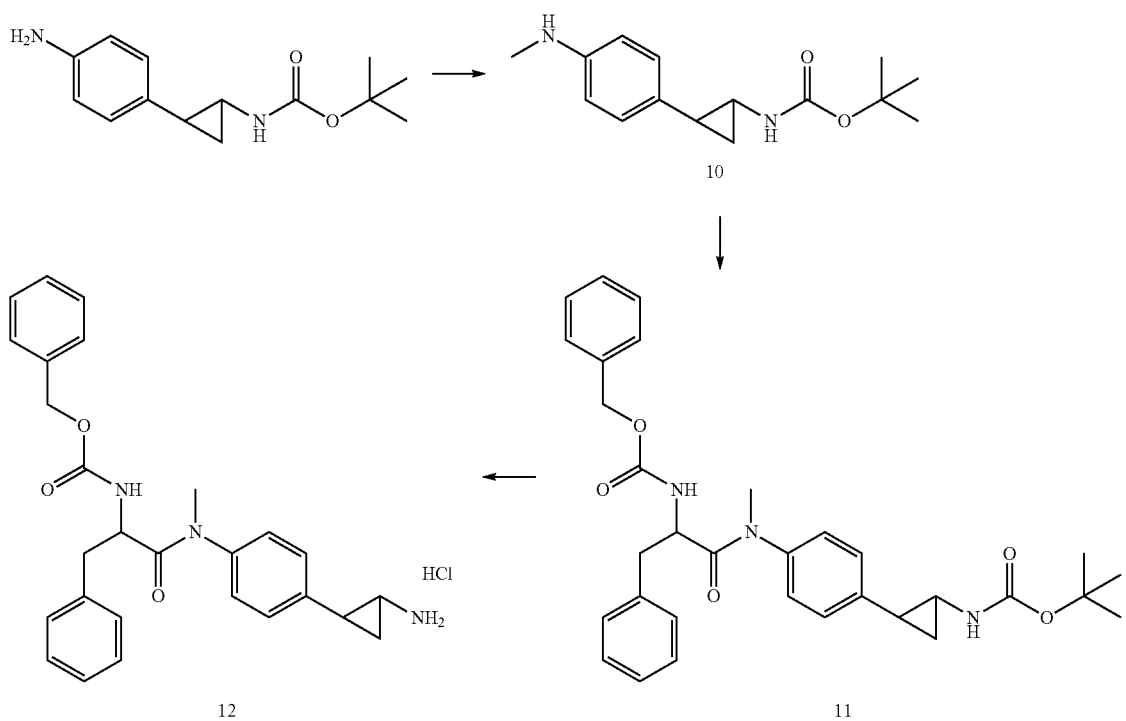

Step a

Synthesis of trans tert-butyl 2-(4-methylaminophenyl)cyclopropyl carbamate (10)

solution of 8-(4-(2-tert-butoxycarbonylaminocyclopropyl)phenylamino)-8-oxooctanoic acid (0.32 mmol, 130 mg) in dry tetrahydrofuran (5 mL), and the mixture was stirred for 10 min. The solid was filtered off, and O-(2-methoxy-2-propyl) hydroxylamine (0.96 mmol, 0.7 mL) was added to the filtrate. The solution was stirred for 15 min at 0° C., then a 6 N HCl solution (10 mL) was added, and the stirring was continued for further 12 h. Therefore the precipitate was filtered and washed with diethyl ether (3×10 mL) to give the pure N¹-(4-(2-aminocyclopropyl)phenyl)-N⁸-hydroxyoctanediamide hydrochloride (9).

¹HNMR (DMSO-d₆, 400 MHz, δ; ppm) δ 1.15-1.17 (m, 1H, CHH cyclopropane), 1.28-1.26 (m, 4H, OCOCH₂CH₂CH₂CH₂CH₂CON), 1.34-1.36 (m, 1H, CHH cyclopropane), 1.49-1.51 (m, 2H, OCOCH₂CH₂CH₂CH₂CH₂CON), 1.52-1.56 (m, 2H, OCOCH₂CH₂CH₂CH₂CH₂CON), 2.26-2.30 (m, 4H, Formaldehyde (1.88 mmol, 0.052 mL), sodium cyanoborohydride (5.64 mmol, 0.356 g) and acetic acid (0.2 mL) were added at 0° C. to a solution of trans tert-butyl 2-(4-aminophenyl)cyclopropyl carbamate (1.88 mmol, 467 mg) in acetonitrile (5 mL). The mixture was stirred at room temperature for 1 h. Water (50 mL) was added, and the mixture was extracted with ethyl acetate (3×50 mL). The organic phases were combined and dried over sodium sulfate, then the solvent was removed under reduced pressure. The residual oil was chromatographed on silica gel eluting with ethyl acetate/n-hexane 1/2 to furnish the compound as yellow oil; 34% yield; ¹H NMR (CDCl₃, 400 MHz, δ; ppm) δ 1.05-1.12 (d, 2H, cyclopropane protons), 1.46 (s, 9H, C(CH₃)₃), 1.94-1.99

(m, 1H, PhCHH), 2.65-2.66 (dd, 1H, PhCHH), 2.83 (s, 3H, NHCH$_3$), 3.62 (bs, 1H, NHCH$_3$), 4.82-4.84 (bs, 1H, NHCO), 6.54-6.57 (d, 2H, aromatic protons), 7.01-7.03 (d, 2H, aromatic protons); $^{13}$C NMR (CDCl3, 400 MHz, δ; ppm) δ 14.40, 22.80, 28.40 (3C), 29.60, 32.60, 79.50, 112.90 (2C), 125.80, 130.1, 146.40, 155.60; MS (ESI) m/z: 262.17 [M]$^+$.

Step b

Synthesis of trans tert-butyl 2-[4-(N-methyl-N-benzyloxycarbonylphenylalanyl) phenyl]cyclopropyl carbamate (11)

Triethylamine (0.61 mmol, 0.08 mL) and PyBOP (0.18 mmol, 0.095 g) were added under N$_2$ atmosphere to a solution of N-benzyloxycarbonylphenylalanine (0.15 mmol, 0.045 g) in dry dimethylformamide (2 mL), and the mixture was stirred over a period of 0.5 h. trans tert-Butyl 2-(4-methylaminophenyl)cyclopropyl carbamate 10 (0.15 mmol, 0.041 g) was added, under N$_2$ atmosphere, and the mixture was stirred overnight. The reaction was poured into water (30 mL) and extracted with ethyl acetate (3×30 mL). The organic layers were washed with saturated sodium chloride solution (3×30 mL), dried with anhydrous sodium sulfate and concentrated. The residue was purified by chromatographic column on silica gel eluting with ethyl acetate/chloroform 1/5 to afford the pure compound as a colorless oil, 72% yield; $^1$H NMR (CDCl$_3$, 400 MHz, δ; ppm) δ 1.20-1.25 (m, 2H, CH$_2$ cyclopropane), 1.46 (s, 9H, C(CH$_3$)$_3$), 2.07-2.09 (m, 1H, PhCH), 2.74-2.77 (m, 1H, CHNH cyclopropane), 2.89-2.94 (m, 1H, PhCHHCH), 3.19 (s, 3H, NCH$_3$), 4.58-4.60 (m, 1H, PhCHHCH), 4.92 (bs, 1H, NHCOOC(CH$_3$)$_3$), 5.01 (s, 2H, PhCH$_2$OCONH), 5.48-5.50 (m, 1H, PhCHHCH), 6.74 (bs, 1H, NHCOOBn), 6.93-6.97 (d, 2H, aromatic protons), 7.00-7.04 (m, 2H, aromatic protons), 7.08-7.10 (m, 2H, aromatic protons), 7.20-7.24 (m, 3H, aromatic protons), 7.33-7.36 (m, 5H, aromatic protons); $^{13}$C NMR (CDCl3, 400 MHz, δ; ppm) δ 14.40, 22.80, 28.40 (3C), 32.60, 36.1, 37.60, 55.90, 66.80, 79.50, 125.20 (2C), 125.90, 127.10 (2C), 127.60, 127.70 (2C), 128.60 (2C), 132.9, 136.1, 136.6, 137.3, 140.8, 155.6, 155.9, 165.0; MS (ESI) m/z: 543.27 [M]$^+$.

Step c

Synthesis of trans benzyl 1-((4-(2-aminocyclopropyl)phenyl)(methyl)amino)-1-oxo-3-phenylpropan-2-ylcarbamate hydrochloride (12)

A 6 N HCl solution (2 mL) was added to a solution of trans tert-butyl 2-[4-(N-methyl-N-benzyloxycarbonylphenylalanyl)phenyl]cyclopropyl carbamate 11 (0.26 mmol, 0.1 g) in tetrahydrofuran (2 mL), and the mixture was stirred for 12 h at room temperature. The precipitated solid was filtered, washed with diethyl ether (3×10 mL) and dried to give the pure compound as a white solid; 82% yield, m.p. 156-158° C., recryst. solvent: benzene; $^1$H NMR (DMSO-d$_6$, 400 MHz, δ; ppm) δ 1.25-1.27 (m, 1H, CHH cyclopropane), 1.43-1.45 (m, 1H, CHH cyclopropane), 2.65-2.67 (m, 1H, PhCH cyclopropane), 2.68-2.70 (m, 1H, CHNH$_3$Cl cyclopropane), 2.70-2.72 (m, 1H, PhCHHCH), 3.14 (s, 3H, NCH$_3$), 3.34-3.36 (m, 1H, PhCHHCH), 4.19-4.22 (m, 1H, PhCHHCH), 4.94 (s, 2H, PhCH$_2$OCONH), 6.71-6.74 (m, 2H, aromatic protons), 7.01-7.32 (m, 12H, aromatic protons), 7.68 (bs, 1H, NHCOOBn), 8.53 (bs, 3H, NH$_3$Cl); $^{13}$C NMR (DMSO-d$_6$, 400 MHz, δ; ppm) δ 12.1, 20.5, 36.1, 37.6, 40.3, 55.9, 66.8, 125.2 (2C), 125.9, 127.1 (2C), 127.6, 127.7 (2C), 128.6 (2C), 128.9 (2C), 132.9, 136.1, 136.6, 137.3, 155.9, 165.0, 140.8; MS (ESI) m/z: 479.19 [M]$^+$.

Example 8

Synthesis of trans N-(4-(2-aminocyclopropyl)phenyl)-2-(3-benzylureido)-3-phenylpropanamide hydrochloride (16)

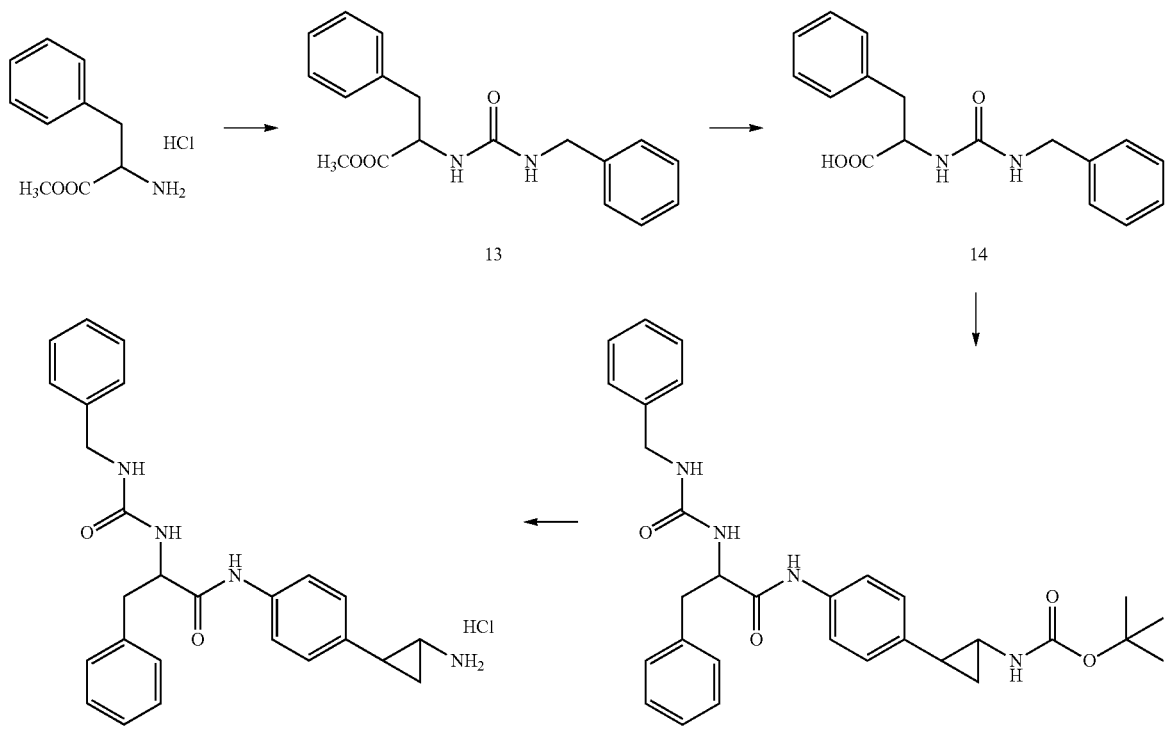

Step a

Synthesis of methyl 2-(3-benzylureido)-3-phenylpropanoate (13)

Triethylamine (1.86 mmol, 0.26 ml) and benzyl isocyanate (1.86 mmol, 0.23 mL) were added at 0° C. to a solution of phenylalanine methylester hydrochloride (0.93 mmol, 0.2 g) in tetrahydrofuran, and the mixture was stirred over a period of 12 h. The reaction was poured into water (30 mL) and extracted with ethyl acetate (5×30 mL). The organic layers were washed with saturated sodium chloride solution (3×30 mL), dried with anhydrous sodium sulfate and concentrated. The residue was purified by chromatographic column on silica gel eluting with ethyl acetate/n-hexane 1/2 to afford the pure compound as a colorless oil, 95% yield; $^1$H NMR (CDCl$_3$, 400 MHz, δ; ppm) δ 2.91-2.92 (dd, 1H, PhCHHCHCOO), 2.96-2.97 (dd, 1H, PhCHHCHCOO), 3.56 (s, 3H, COOCH$_3$), 4.70-4.71 (m, 1H, PhCHHCHCOO), 4.17-4.19 (dd, 1H, PhCHHNHCONH), 4.22-4.24 (dd, 1H, PhCHHNHCONH), 5.46 (bs, 2H, NHCONH), 7.03-7.04 (2H, aromatic protons), 7.17-7.25 (m, 8H, aromatic protons); $^{13}$C NMR (CDCl$_3$, 400 MHz, δ; ppm) δ 36.3, 44.4, 51.9, 57.3, 125.9, 126.7, 126.9 (2C), 127.7 (2C), 128.5 (2C), 128.6 (2C), 136.6, 137.9, 157.9, 171.5; MS (ESI) m/z: 312.14 [M]$^+$.

Step b

Synthesis of 2-(3-benzylureido)-3-phenylpropanoic acid (14)

A solution of ethyl 2-(3-benzylureido)-3-phenylpropanoate 13 (2.66 mmol, 0.83 g) and 2 N lithium hydroxide (5.32 mmol, 0.22 g) in ethanol (20 mL) was kept in stirring overnight at room temperature. The reaction was quenched by addition of 2 N HCl until pH=2, afterwards the precipitate was filtered, washed with water (3×30 mL) and dried to obtain the pure 2-(3-benzylureido)-3-phenylpropanoic acid as a pale white solid; 95% yield, m.p. 115-117° C.; recryst. solvent: cyclohexane/benzene; $^1$H NMR (CDCl$_3$, 400 MHz, δ; ppm) δ 2.85-2.87 (dd, 1H, PhCHHCHCOO), 2.89-2.91 (dd, 1H, PhCHHCOO), 4.38-4.40 (m, 1H, PhCHHCHCOO), 6.14-6.17 (d, 1H, PhCHHNHCONH), 6.54-6.57 (m, 1H, PhCHHNHCONH), 7.18-7.30 (m, 10H, aromatic protons), 12.65 (bs, 1H, COOH); $^{13}$C NMR (CDCl3, 400 MHz, δ; ppm) δ 36.0, 44.4, 56.8, 125.9, 126.7, 126.9 (2C), 127.7 (2C), 128.5 (2C), 128.6 (2C), 136.6, 137.9, 157.6, 174.7; MS (ESI) m/z: 298.32 [M]$^+$.

Step c

Synthesis of trans tert-butyl 2-[4-[2-(3-benzylureido)-3-phenylpropanoyl]aminophenyl]cyclopropyl carbamate (15)

Triethylamine (1.92 mmol, 0.27 mL) and PyBOP (0.57 mmol, 0.30 g) were added under N$_2$ atmosphere to a solution of 2-(3-benzylureido)-3-phenylpropanoic acid (0.48 mmol, 0.14 g) in dry dimethylformamide (2 mL), and the mixture was stirred for 0.5 h. tert-Butyl (2-(4-aminophenyl)cyclopropyl)carbamate (0.52 mmol, 0.13 g) was added, under N$_2$ atmosphere, and the stirring was continued overnight. The reaction was poured into water (30 mL) and extracted with ethyl acetate (3×30 mL). The organic layers were washed with saturated sodium chloride solution (3×30 mL), dried with anhydrous sodium sulfate and concentrated. The residue was purified by chromatographic column on silica gel eluting with ethyl acetate/n-hexane 1/1 to afford the pure compound 15 as white solid, 70% yield; m.p. 100-102° C.; recrist. solvent: cyclohexane $^1$H NMR (CDCl3, 400 MHz, δ; ppm) δ 1.09-1.10 (m, 1H, CHH cyclopropane), 1.18-1.19 (m, 1H, CHH cyclopropane), 1.46 (s, 9H, C(CH3)3), 2.30-2.31 (m, 1H, PhCH cyclopropane), 2.52-2.54 (m, 1H, CHNH cyclopropane), 2.98-3.00 (dd, 1H, PhCHHCHCOO), 3.01-3.02 (dd, 1H, PhCHHCHCOO), 4.18-4.20 (m, 2H, PhCHHCHCOO), 4.27-4.28 (m, 1H, PhCHHNHCONH), 4.89 (bs, 1H, NHCOOC(CH3)3), 4.92-4.94 (d, 1H, PhCHHNHCONH), 6.05-6.07 (m, 1H, PhCHHNHCONH), 6.75-6.77 (m, 1H, PhCHHNHCONH), 6.90-6.94 (d, 2H, aromatic protons), 7.10-7.27 (m, 12H, aromatic protons), 9.23 (bs, 1H, PhNHCOCH); $^{13}$C NMR (CDCl$_3$, 400 MHz, δ; ppm) δ 14.40, 22.80, 28.40 (3C), 32.60, 36.90, 44.4, 59.0, 79.50, 121.0 (2C), 125.20 (2C), 125.90, 126.7, 126.9 (2C), 127.70 (2C), 128.5 (2C), 128.60 (2C), 134.90, 136.60, 137.3, 137.9, 155.6, 157.60, 172.70; MS (ESI) m/z: 528.27 [M]$^+$.

Step d

Synthesis of trans N-(4-(2-aminocyclopropyl)phenyl)-2-(3-benzylureido)-3-phenylpropanamide hydrochloride (16)

A 6 N HCl aqueous solution (2 mL) was added to a solution of trans tert-butyl 2-[4-[2-(3-benzylureido)-3-phenylpropanoyl]aminophenyl]cyclopropyl carbamate (0.30 mmol, 0.1 g) in tetrahydrofuran (2 mL), and the mixture was stirred for 12 h at room temperature. The precipitated solid was filtered, washed with diethyl ether (3×10 mL) and dried to give the pure compound 16 as a white solid; 82% yield, m.p. 153-155° C., recryst. solvent: benzene; $^1$H NMR (DMSO-d$_6$, 400 MHz, δ; ppm) δ 1.10-1.11 (m, 1H, CHH cyclopropane), 1.20-1.21 (m, 1H, CHH cyclopropane), 2.30-2.32 (m, 1H, PhCH cyclopropane), 2.43-2.45 (m, 1H, CHNH$_3$Cl cyclopropane), 2.91-2.92 (dd, 1H, PhCHHCHCOO), 2.96-2.97 (dd, 1H, PhCHHCHCOO), 4.17-6.19 (m, 1H, PhCHHNHCONH), 4.20-4.22 (d, 1H, PhCHHNHCONH), 4.70-4.71 (m, 1H, PhCHHCHCOO), 6.32-6.34 (m, 1H, PhCHHNHCONH), 6.55-6.56 (m, 1H, PhCHHNHCONH), 7.04-7.05 (d, 2H, aromatic protons), 7.10-7.27 (m, 10H, aromatic protons), 7.49-7.51 (d, 2H, aromatic protons), 8.34 (bs, 3H, CHNH$_3$Cl), 10.08 (bs, 1H, PhNHCOCH); $^{13}$C NMR (DMSO-d$_6$, 400 MHz, δ; ppm) δ 12.1, 20.5, 36.9, 40.3, 44.4, 59.0, 121.0 (2C), 125.9, 125.2 (2C), 126.7, 126.9 (2C), 127.7 (2C), 128.5 (2C), 128.6 (2C), 134.9, 136.6, 137.3, 137.9, 157.6, 172.7; MS (ESI) m/z: 464.19 [M]$^+$.

2. BIOLOGICAL TESTING

Methods

Human recombinant MAO A and MAO B were expressed in *Pichia pastoris* and purified as published (Binda C, et al., *Proc. Natl. Acad. Sci. USA* 100: 9750-9755, 2003) Inhibition assays and K$_i$ values were measured using kynuramine (MAO A) and benzylamine (MAO B) as substrates at pH 7.5 according to published procedures (Binda C, et al., *Proc. Natl. Acad. Sci. USA* 100: 9750-9755, 2003). Mouse recombinant LSD2 was expressed in *E. coli* and purified as described (Karytinos A, et al., *J. Biol. Chem.* 284:17775-17782, 2009). Human recombinant LSD1/CoREST were expressed in *E. coli* as separate proteins and co-purified following previously reported procedures (Forneris F, et al. *Trends Biochem Sci* 33:181-189, 2008). Enzymatic activities and inhibition assays with both demethylases were carried out at pH 7.5-8.0 using a methylated H3 peptide (Forneris F, et al., *J. Biol.*

Chem. 282: 20070-20074 2007, Karytinos A, et al., *J. Biol. Chem.* 284:17775-17782, 2009).

Compounds were screened for their potential effect on enzymatic activity by a peroxidase-coupled assay at 25° C. using non-saturating substrate concentrations. Apparent $k_{cat}$ values measured in the presence of a compound (final concentration ranging from 25 µM to 150 µM, depending on the solubility) are compared with that of a reference assay performed in the absence of the tested compound, Table 6.

LSD1 activities were assayed in 50 mM Hepes/NaOH pH 7.5 using a histone H3 peptide mono-methylated at Lys4 as substrate. LSD2 activities were measured in 50 mM Hepes/NaOH pH 8.0 with the substrate histone H3 peptide di-methylated at Lys4, Table 6. MAO A and MAO B assays were performed in 50 mM Hepes/NaOH pH 7.5, 0.5% (v/v) reduced Triton X-100 by using kynuramine and benzylamine, respectively, as substrate, Table 6.

NB4 cells were treated at different concentrations of 6e (FIG. 1). 6e and retinoic acid (RA, Sigma) were dissolved in DMSO at 1000× concentration. NB4 cells were grown in RPMI medium, supplemented with 10% FBS, 100 U/ml penicilline, 100m/ml streptomycine, and maintained in a humidified incubator at 37° C., 10% O2 and 5% CO2. Cells were plated at a 150.000/ml density and treated with RA (10 nM, 100 nM and 1 µM) in presence or absence of 2 µM 6e. In vehicle-treated cells DMSO was added at a final concentration of 0.2%. At each time point (2, 4 and 7 days), cells were collected, stained with a trypan blue solution and counted using a hemocytometer. Only viable cells were scored. In parallel, cells were cyto-spun on a glass-slide, air dried and stained with the May Grunwald-Giemsa method.

Results

Tranylcypromine is a covalent inhibitor of MAOs and LSDs and its binding causes a bleaching of the protein-bound flavin absorbance that can be easily measured (Li M, Hubalek F, Restelli N, Edmondson D E, Mattevi A. Insights into the mode of inhibition of human mitochondrial monoamine oxidase B from high-resolution crystal structures. *Proc Natl Acad Sci USA* 100:9750-9755, 2003; Schmidt D M, McCafferty D G. trans-2-Phenylcyclopropylamine is a mechanism-based inactivator of the histone demethylase LSD1. *Biochemistry* 46:4408-4416, 2007; Karytinos A, Forneris F, Profumo A, Ciossani G, Battaglioli E, Binda C, Mattevi A. A novel mammalian flavin-dependent histone demethylase *J Biol Chem* 284:17775-17782, 2009). This feature provided a tool for a rapid and efficient screening of the tranylcypromine derivatives of the present invention. Each compound was further evaluated by measuring the effect on enzymatic activities as reported in Table 6. Ki values calculated for selected compounds are reported in Table 7.

TABLE 6

Activity profile of representative compounds of the invention

| Compound | LSD1[a,b] | LSD2[a,b] | MAO A[a,c] | MAO B[a,c] |
|---|---|---|---|---|
| 5a | + | + | + | + |
| 5b | + | + | + | + |
| 5c | + | + | + | + |
| 5d | + | + | + | + |
| 5e | − | − | + | − |
| 5f | + | + | + | + |
| 5g | + | + | + | + |
| 5h | + | + | + | − |
| 6a | + | + | + | − |
| 6b | + | + | + | − |
| 6c | + | + | + | − |
| 6d | + | + | + | − |

TABLE 6-continued

Activity profile of representative compounds of the invention

| Compound | LSD1[a,b] | LSD2[a,b] | MAO A[a,c] | MAO B[a,c] |
|---|---|---|---|---|
| 6e | + | + | + | − |
| 6f | + | ND | ND | ND |
| 6g | + | + | + | − |
| 6h | + | + | + | − |
| 6i | + | + | + | − |
| 6j | + | + | + | − |
| 6k | − | − | − | − |
| 6l | + | + | + | − |
| 6m | + | + | + | − |
| 7 | + | + | + | − |
| 8 | + | + | + | − |
| 9 | + | + | ND | + |
| 12 | + | + | + | − |
| 16 | + | + | + | + |

[a]No inhibition is indicated as "−", whereas inhibition is described by "+". Maximum inhibitor concentrations used for inhibition studies were 1 mM or the concentrations corresponding to inhibitor-saturated solutions for inhibitors with <1 mM solubility.
[b]LSD1 activities were assayed in 50 mM Hepes/NaOH pH 7.5 using a histone H3 peptide mono-methylated at Lys4 as substrate. LSD2 activities were measured in 50 mM Hepes/NaOH pH 8.0 with the substrate histone H3 peptide di-methylated at Lys4.
[c]MAO A and MAO B assays were performed in 50 mM Hepes/NaOH pH 7.5, 0.5% (v/v) reduced Triton X-100 by using kynuramine and benzylamine, respectively, as substrate.

TABLE 7

Inhibition of selected compounds of the invention against LSD1, LSD2 and Monoamine Oxidases.

| Compound | LSD1[a,b] Ki (µM) | LSD2[a,b] Ki (µM) | MAO A[a,c] Ki (µM) | MAO B[a,c] Ki (µM) |
|---|---|---|---|---|
| 5a | 1.9 µM | 20 | 0.5 | 7.4 |
| 5b | 1.1 | 61 | 2.3 | 3.5 |
| 6e | 1.3 | 38.0 | 12.5[e] | no inhibition[d] |
| 6l | 40 | 12 | 49 | no inhibition[d] |
| 7 | 3.3 | ND | ND | no inhibition[d] |
| 8 | 2.1 | 20 | 4.0 | no inhibition[d] |
| 12 | 34 | ND | 19 | no inhibition[d] |
| 16 | 18 | ND | ND | ND |

[a]Enzymatic activity were measured at 25° C. using the peroxidase-coupled assay. Errors in the determination of Ki are within 30% of their values; ND, not determined The Ki values were determined by steady-state competition experiments. The slow rate of irreversible inhibition allowed these experiments to be performed by normal steady-state approaches.
[b]LSD1 activities were assayed in 50 mM Hepes/NaOH pH 7.5 using a histone H3 peptide mono-methylated at Lys4 as substrate. LSD2 activities were measured in 50 mM Hepes/NaOH pH 8.0 with the substrate histone H3 peptide di-methylated at Lys4.
[c]MAO A and MAO B assays were performed in 50 mM Hepes/NaOH pH 7.5, 0.5% (v/v) reduced Triton X-100 by using kynuramine and benzylamine, respectively, as substrate.
[d]No detectable inhibition at the maximum tested concentrations, corresponding to inhibitor saturated solutions.
[e]The Ki value was re-determined using improved MAO A preparations resulting in a slightly different value from that published in Binda C, et al., *J. Am. Chem. Soc.*. 132: 6827-6833, 2010

Compound 6e was further evaluated in for its biological activity in NB4 cells (FIG. 1). NB4 cells were treated at different concentrations of 6e Interestingly, while not effective per se, 6e was able to strongly potentiate the differentiating effect of RA. This was observed at RA concentrations as low as 10 nM, that are almost totally ineffective in the absence of 6e. The combination of RA and 6e at all doses tested cooperatively inhibited cell growth and led to an enhanced differentiation, as shown in the representative cytospins of FIG. 1. Similar effect is shown when ability to induce cell apoptosis in NB4 cells was measured (FIG. 2). The effect of 6e was to increase the efficacy of retinoic acid to induce apoptosis.

The invention claimed is:
1. A compound of the general formula (I)

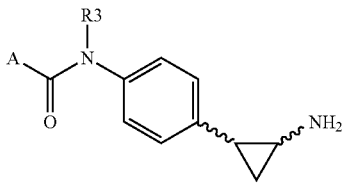

(I)

or a stereoisomer, tautomer, racemic form, enantiomer, diastereomer, epimer, polymorph, solvate, mixtures thereof, prodrug, pharmaceutically acceptable salt thereof, wherein:

A is R or $CH(R_1)$—NH—CO—$R_2$;

R and $R_2$ are selected from the group consisting of alkyl, alkenyl, alkynyl, cycloalkyl, aryl, heteroaryl, heterocycloalkyl, cycloalkylalkyloxy, arylalkyloxy, heteroarylalkyloxy, heterocycloalkylalkyloxy, cycloalkylalkyl, arylalkyl, heteroarylalkyl, heterocycloalkylalkyl, cycloalkylalkylamino, arylalkylamino, heteroarylalkylamino, and heterocycloalkylalkylamino;

$R_1$ is selected from the group consisting of alkyl, alkenyl, alkynyl, cycloalkyl, aryl, heteroaryl, heterocycloalkyl, cycloalkylalkyl, arylalkyl, heteroarylalkyl, and heterocycloalkylalkyl; and $R_3$ is H, or lower alkyl.

2. The compound as claimed in claim 1, wherein:
A is R; and
$R_3$ is H.

3. The compound as claimed in claim 2, wherein:
R is alkyl, aryl, arylalkyloxy, arylalkyl, or any of which may be optionally substituted.

4. The compound as claimed in claim 1, wherein:
A is $CH(R_1)$—NH—CO—$R_2$; and
$R_3$ is H.

5. The compound as claimed in claim 1, wherein:
A is $CH(R_1)$—NH—CO—$R_2$; and
$R_3$ is —$CH_3$.

6. The compound as claimed in claim 4, wherein, independently or in any combination:
$R_1$ is alkyl, aryl, heteroaryl, cycloalkylalkyl, arylalkyl, heteroarylalkyl, or any of which may be optionally substituted; and
$R_2$ is arylalkyloxy, heteroarylalkyloxy, arylalkylamino, or any of which may be optionally substituted.

7. The compound of claim 1, belonging to the following group:
trans benzyl 4-(2-aminocyclopropyl)phenylcarbamate;
trans N-(4-(2-aminocyclopropyl)phenyl)benzamide;
trans N-(4-(2-aminocyclopropyl)phenyl)-1-naphthamide;
trans N-(4-(2-aminocyclopropyl)phenyl)-2-naphthamide;
trans N-(4-(2-aminocyclopropyl)phenyl)biphenyl-4-carboxamide;
trans N-(4-(2-aminocyclopropyl)phenyl)-2-phenylacetamide;
trans N-(4-(2-aminocyclopropyl)phenyl)-2-(naphthalen-1-yl)acetamide;
trans N-(4-(2-aminocyclopropyl)phenyl)-2-(naphthalen-2-yl)acetamide;
trans benzyl 1-(4-(2-aminocyclopropyl)phenylamino)-3-methyl-1-oxobutan-2-ylcarbamate;
trans benzyl 1-(4-(2-aminocyclopropyl)phenylamino)-4-methyl-1-oxopentan-2-ylcarbamate;
trans benzyl 1-(4-(2-aminocyclopropyl)phenylamino)-3-cyclohexyl-1-oxopropan-2-ylcarbamate;
trans benzyl 2-(4-(2-aminocyclopropyl)phenylamino)-2-oxo-1-phenylethylcarbamate;
trans benzyl 1-(4-(2-aminocyclopropyl)phenylamino)-1-oxo-3-phenylpropan-2-ylcarbamate;
trans benzyl 1-(4-(2-aminocyclopropyl)phenylamino)-3-(4-bromophenyl)-1-oxopropan-2-ylcarbamate;
trans benzyl 1-(4-(2-aminocyclopropyl)phenylamino)-3-(4-methoxyphenyl)-1-oxopropan-2-ylcarbamate;
trans benzyl 1-(4-(2-aminocyclopropyl)phenylamino)-1-oxo-4-phenylbutan-2-ylcarbamate;
trans benzyl 1-(4-(2-aminocyclopropyl)phenylamino)-1-oxo-3,3-diphenylpropan-2-ylcarbamate;
trans benzyl 1-(4-(2-aminocyclopropyl)phenylamino)-3-(naphthalen-1-yl)-1-oxopropan-2-ylcarbamate;
trans benzyl 1-(4-(2-aminocyclopropyl)phenylamino)-3-(naphthalen-2-yl)-1-oxopropan-2-ylcarbamate;
trans benzyl 1-(4-(2-aminocyclopropyl)phenylamino)-4-(1H-indol-3-yl)-1-oxobutan-2-ylcarbamate;
trans benzyl 1-(4-(2-aminocyclopropyl)phenylamino)-4-(benzo[b]thiophen-3-yl)-1-oxobutan-2-ylcarbamate;
trans 4-bromobenzyl 1-(4-(2-aminocyclopropyl)phenylamino)-1-oxo-3-phenylpropan-2-ylcarbamate;
cis benzyl 1-(4-(2-aminocyclopropyl)phenylamino)-1-oxo-3-phenylpropan-2-ylcarbamate;
trans $N^1$-(4-(2-aminocyclopropyl)phenyl)-$N^8$-hydroxyoctanediamide;
trans benzyl 1-((4-(2-aminocyclopropyl)phenyl)(methyl)amino)-1-oxo-3-phenylpropan-2-ylcarbamate;
trans N-(4-(2-aminocyclopropyl)phenyl)-2-(3-benzylureido)-3-phenylpropanamide;

or a isomer, tautomer, racemic form, enantiomer, diastereomer, epimer, polymorph, solvate, mixtures thereof, prodrug, or pharmaceutically acceptable salts thereof.

8. Process for the preparation of a compound of general formula (I) as defined in claim 1, wherein A is R, the process comprising:
(a) reacting a compound of formula (II) with an acylating agent to give a compound of formula (III)

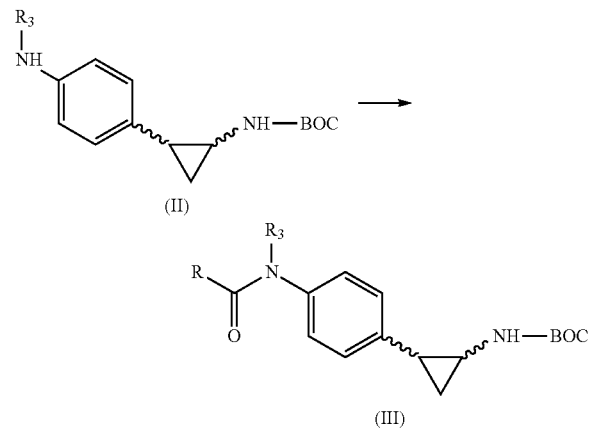

wherein R is selected from the group consisting of alkyl, alkenyl, alkynyl, cycloalkyl, aryl, heteroaryl, heterocycloalkyl, cycloalkylalkyloxy, arylalkyloxy, heteroarylalkyloxy, heterocycloalkylalkyloxy, cycloalkylalkyl, arylalkyl, heteroarylalkyl, heterocycloalkylalkyl, cycloalkylalkylamino, arylalkylamino, heteroarylalkylamino, and heterocycloalkylalkylamino;

$R_3$ is H, or lower alkyl; and

Boc is the tert-butyloxycarbonyl protecting group; and (b) optionally converting the compound of formula (III) obtained in a) into another compound of formula (III), removing the Boc protecting group from the compound of formula (III) to obtain the compound of formula (I):

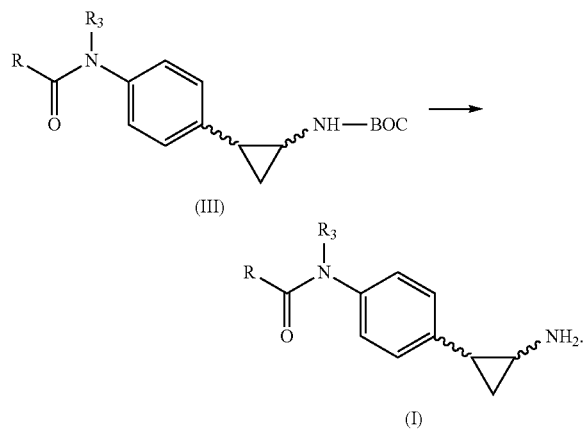

9. Process for the preparation of a compound of general formula (I), as claimed in claim 1, wherein A is CH($R_1$)—NH—CO—$R_2$, the process comprising:

(a) reacting a compound of formula (II) with an acylating agent to give a compound of formula (IV)

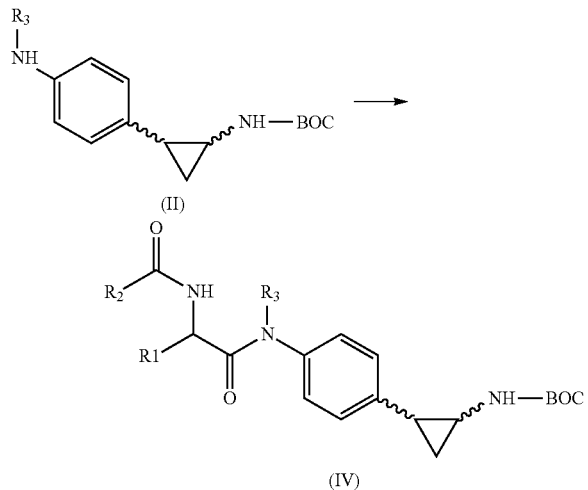

wherein $R_1$ is selected from the group consisting of alkyl, alkenyl, alkynyl, cycloalkyl, aryl, heteroaryl, heterocycloalkyl, cycloalkylalkyl, arylalkyl, heteroarylalkyl, and heterocycloalkylalkyl;

$R_2$ is selected from the group consisting of alkyl, alkenyl, alkynyl, cycloalkyl, aryl, heteroaryl, heterocycloalkyl, cycloalkylalkyloxy, arylalkyloxy, heteroarylalkyloxy, heterocycloalkylalkyloxy, cycloalkylalkyl, arylalkyl, heteroarylalkyl, heterocycloalkylalkyl, cycloalkylalkylamino, arylalkylamino, heteroarylalkylamino, and heterocycloalkylalkylamino; and $R_3$ is H, or lower alkyl; and Boc is the tert-butyloxycarbonyl protecting group; and (b) optionally converting the compound of formula (IV) obtained in a) into another compound of formula (IV), removing the Boc protecting group from the compound of formula (IV) to obtain the compound of formula (I):

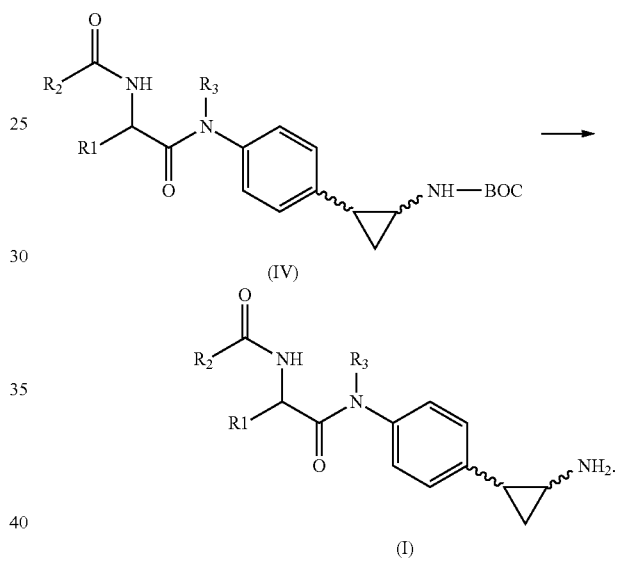

10. The compound according to claim 1 being an inhibitor of LSD1 and/or LSD2 histone demethylase.

11. A pharmaceutical composition comprising an effective amount of one or more compounds of general formula (I), according to claim 1, alone or in combination with other active compounds, and at least one pharmaceutically acceptable excipient.

12. The pharmaceutical composition of claim 11 being formulated in unit dosage form.

* * * * *